United States Patent
Landy, III et al.

(10) Patent No.: US 12,268,628 B2
(45) Date of Patent: Apr. 8, 2025

(54) FLUID TEMPERATURE CONTROL SYSTEM

(71) Applicant: Belmont Instrument, LLC, Billerica, MA (US)

(72) Inventors: John Joseph Landy, III, Billerica, MA (US); Alexander Rick, Derry, NH (US); Tristan Dion, Hudson, NH (US); Skylar Nesheim, Brighton, MA (US); David Dumais, Billerica, MA (US); Yeu Wen Tseng, Watertown, MA (US); Chuong Vu, Revere, MA (US); Robert Charles Shea, Reading, MA (US)

(73) Assignee: Belmont Instrument, LLC, Billerica, MA (US)

( * ) Notice: Subject to any disclaimer, the term of this patent is extended or adjusted under 35 U.S.C. 154(b) by 0 days.

(21) Appl. No.: 18/228,177

(22) Filed: Jul. 31, 2023

(65) Prior Publication Data

US 2024/0000606 A1    Jan. 4, 2024

Related U.S. Application Data

(63) Continuation of application No. 16/937,888, filed on Jul. 24, 2020, now Pat. No. 11,759,351.

(Continued)

(51) Int. Cl.
*A61F 7/00*    (2006.01)
*A61F 7/08*    (2006.01)

(52) U.S. Cl.
CPC ............ *A61F 7/0085* (2013.01); *A61F 7/007* (2013.01); *A61F 7/0097* (2013.01); *A61F 7/08* (2013.01);

(Continued)

(58) Field of Classification Search
CPC .................... A61F 7/0085; A61F 7/007; A61F 2007/0056; A61F 2007/0071
See application file for complete search history.

(56) References Cited

U.S. PATENT DOCUMENTS

| | | | |
|---|---|---|---|
| 4,309,592 A | 1/1982 | Le Boeuf | |
| 4,532,414 A | 7/1985 | Shah et al. | |

(Continued)

FOREIGN PATENT DOCUMENTS

| | | |
|---|---|---|
| CN | 1701821 A | 11/2005 |
| CN | 2897246 Y | 5/2007 |

(Continued)

OTHER PUBLICATIONS

Internationl Search Report for PCT/US2020/043425 (6 pages) mailed Oct. 16, 2020.

(Continued)

*Primary Examiner* — Tigist S Demie
(74) *Attorney, Agent, or Firm* — Choate, Hall & Stewart LLP; William R. Haulbrook; Peter A. Flynn

(57) ABSTRACT

Described herein is a system for heating and/or cooling a fluid that includes a temperature forcing device having a bottom plate and a top plate hingedly coupled to the bottom plate. At least one of the bottom plate and the top plate has a recess or other area for receiving at least one flexible fluid holder (e.g., a polymer bag). The bottom plate and/or top plate also has at least one protrusion and/or recession in its interior wall(s) such that a fluid passageway in the flexible fluid holder is defined when the fluid holder is placed between the top and bottom plates, and the plates are closed together. The fluid holder then has a fluid inlet for receiving the fluid to be heated and/or cooled and a fluid outlet for delivering the fluid. The fluid, upon being heated and/or cooled by the temperature forcing device, may then be (Continued)

Bar Forms Fluid Path in Disposable Bag when Device is Closed

No Fluid Path is Defined when Device is Open delivered to a patient or may be delivered to another system component, e.g., for additional heating/cooling.

16 Claims, 15 Drawing Sheets

Related U.S. Application Data

(60) Provisional application No. 62/948,717, filed on Dec. 16, 2019, provisional application No. 62/891,156, filed on Aug. 23, 2019, provisional application No. 62/888,301, filed on Aug. 16, 2019.

(52) U.S. Cl.
CPC ............... *A61F 2007/0056* (2013.01); *A61F 2007/0071* (2013.01)

(56) References Cited

U.S. PATENT DOCUMENTS

| | | | |
|---|---|---|---|
| 4,680,445 A * | 7/1987 | Ogawa | A61M 5/44 392/479 |
| 4,906,816 A | 3/1990 | van Leerdam | |
| 6,500,200 B1 | 12/2002 | Kushnir | |
| 6,508,831 B1 | 1/2003 | Kushnir | |
| 11,759,351 B2 | 9/2023 | Landy, III et al. | |
| 2002/0032473 A1 | 3/2002 | Kushnir et al. | |
| 2003/0114795 A1 | 6/2003 | Faries et al. | |
| 2004/0079089 A1 * | 4/2004 | Wallach | A61M 5/44 607/105 |
| 2007/0051409 A1 | 3/2007 | Landy et al. | |
| 2008/0097562 A1 | 4/2008 | Tan | |
| 2009/0043256 A1 | 2/2009 | Landy et al. | |
| 2009/0192446 A1 | 7/2009 | Landy, III et al. | |
| 2010/0244349 A1 | 9/2010 | Moutafis | |
| 2010/0280582 A1 | 11/2010 | Baker et al. | |
| 2011/0125232 A1 | 5/2011 | Landy et al. | |
| 2011/0196302 A1 | 8/2011 | Gildersleeve et al. | |
| 2012/0158103 A1 | 6/2012 | Bledsoe | |
| 2014/0172050 A1 | 6/2014 | Dabrowiak | |
| 2014/0216994 A1 | 8/2014 | Ki | |
| 2015/0190274 A1 | 7/2015 | Landy et al. | |
| 2015/0230973 A1 | 8/2015 | Dabrowiak et al. | |
| 2016/0022478 A1 | 1/2016 | Schaefer et al. | |
| 2016/0082173 A1 * | 3/2016 | Coll | A61M 1/155 604/114 |
| 2016/0101228 A1 | 4/2016 | Landy, III et al. | |
| 2018/0147368 A1 | 5/2018 | Landy, III et al. | |
| 2018/0147369 A1 | 5/2018 | Landy, III et al. | |
| 2018/0147370 A1 | 5/2018 | Landy, III et al. | |
| 2018/0207024 A1 | 7/2018 | Dabrowiak et al. | |
| 2018/0214302 A1 | 8/2018 | Dabrowiak et al. | |
| 2018/0333295 A1 | 11/2018 | Landy et al. | |
| 2020/0001022 A1 | 1/2020 | Landy, III et al. | |

FOREIGN PATENT DOCUMENTS

| | | |
|---|---|---|
| CN | 101631521 A | 1/2010 |
| CN | 103338730 A | 10/2013 |
| CN | 103608059 A | 2/2014 |
| CN | 103826671 A | 5/2014 |
| CN | 106344990 A | 1/2017 |
| CN | 206518654 U | 9/2017 |
| CN | 108136109 A | 6/2018 |
| CN | 109498917 A | 3/2019 |
| CN | 110025859 A | 7/2019 |
| EP | 0726080 A2 | 8/1996 |
| JP | 09-012098 | 1/1997 |
| WO | WO-1999/044552 A1 | 9/1999 |
| WO | WO-2000/062726 A1 | 10/2000 |
| WO | WO-2001/017470 A1 | 3/2001 |
| WO | WO-2011/005986 A2 | 1/2011 |
| WO | WO-2011015912 A1 | 2/2011 |
| WO | WO-2012/168451 A1 | 12/2012 |
| WO | WO-2017/055444 A1 | 4/2017 |
| WO | WO-2018/102354 A1 | 6/2018 |
| WO | WO-2021/034446 A1 | 2/2021 |

OTHER PUBLICATIONS

Written Opinion for PCT/US2020/043425 (11 pages), mailed Oct. 16, 2020.

* cited by examiner

Front View of Machine

Side View of Machine

Top View of Machine when Closed

Disposable Bag with Fluid Path
(Formed by Machine when Closed) Shown

Disposable Bag Shown in Normal State with No Fluid Path Defined. This is how the Bag would be Outside of the Machine.

FLUID TEMPERATURE CONTROL SYSTEM

RELATED APPLICATIONS

This application claims priority to U.S. Provisional Application No. 62/888,301 filed on Aug. 16, 2019, U.S. Provisional Application No. 62/891,156 filed on Aug. 23, 2019, and U.S. Provisional Application No. 62/948,717 filed on Dec. 16, 2019, the entire contents of each of which are hereby incorporated by reference.

FIELD

The subject matter described herein relates to systems and methods for heating and cooling fluids, particularly for use in health care.

BACKGROUND

In modern health care systems and treatment methodologies, therapeutic fluids such as blood, saline, crystalloids, and dialysate often require a temperature adjustment (heating and/or cooling) prior to being delivered to a patient. Treatments sometimes include adjustments of patient's body temperature using temperature management devices. Temperature adjustments are often performed by using a resistance heater to warm a heat transfer fluid and a refrigeration system to cool the same heat transfer fluid as required. The heat transfer fluid may then be pumped through a heat exchanger where the thermal energy is transferred into or out of the therapeutic fluid and/or temperature management device.

Other systems may utilize a solid-state heater/cooler device to perform both the heating function as well as the cooling function, via the heat transfer fluid. In these systems, the heat transfer fluid is pumped to the heat exchanger where the thermal energy is transferred to the therapeutic fluid.

One disadvantage of these methods and systems is that the heat transfer fluid typically operates at temperatures at (or near) the normothermic temperature (i.e., 98.6 degrees Fahrenheit), which makes it particularly susceptible to the growth, incubation, and proliferation of bacteria, thereby exposing the patient to increased risk of infection. For such methods and systems, high temperature (e.g., temperature higher than 121° C.) and/or a disinfecting solution is needed to limit growth, which can cause damage to machines.

Another disadvantage of existing systems is the incidental mixing of the heat transfer fluid with the therapeutic fluid, which may result in bacterial contamination of the system and/or increased risk to the patient. In addition, existing fluid heating systems may employ flexible bags that contain fluid passageways defined by welded channels in the form of a serpentine fluid path. Existing systems may also warm blood by inserting blood via a cartridge into a closed, narrow, slotted chamber. Due to the closed nature of such narrow, slotted chambers, cleaning and fluid leakage detection may be difficult, resulting in sterilization challenges. Additionally, as existing fluid heating systems may not be able to open easily, it is challenging to visualize whether cleaning is necessary.

SUMMARY OF THE INVENTION

Described herein is a system for heating and/or cooling a fluid that includes a temperature forcing device having a bottom plate and a top plate hingedly coupled to the bottom plate. At least one of the bottom plate and the top plate has a recess or other area for receiving at least one fluid holder. The system also includes at least one flexible fluid holder. In certain embodiments, the flexible fluid holder comprises a plastic bag comprising polyvinyl chloride (PVC) and/or other polymer(s) such as ethylene vinyl acetate (EVAM), polypropylene, and/or copolyester ether, for example. The fluid holder has a fluid inlet for receiving the fluid to be heated and/or cooled and a fluid outlet for delivering the fluid. The fluid, upon being heated and/or cooled by the temperature forcing device, may then be delivered to a patient or may be delivered to another system component, e.g., for additional heating/cooling. In some embodiments, the system component directly, physically contacts the body of a patient for managing a body temperature of the patient. For example, in some embodiments, the system component is a blanket, wrap, or mattress containing the fluid. In some embodiments, the fluid is a therapeutic fluid. For example, in some embodiments, the fluid is a therapeutic fluid and the system operates without the need for a heat transfer fluid. In some embodiments, the fluid is a heat transfer fluid. In some embodiments, the fluid being heated and/or cooled (e.g., the therapeutic fluid or the heat transfer fluid) does not directly contact the temperature forcing device such that the temperature forcing device has less risk of harboring pathogens within a healthcare environment. In some embodiments, the fluid path and remaining fluid can be entirely disposed, thereby reducing risk of contamination of the temperature forcing device.

In some embodiments, the top plate and/or the bottom plate include(s) at least one recession and/or at least one protrusion for creating a fluid passageway between the top plate and the bottom plate upon closure of the device. Closure means the top plate and bottom plate are brought into proximity of each other (e.g., touching or not touching) via a hinge coupling the top and bottom plates. In the closed position, the top and bottom plates may touch each other along an edge, protrusion, and/or at another/other location(s). Upon closure of the device, a fluid passageway is defined in the flexible fluid holder by the at least one recession and/or at least one protrusion in (an) interior wall(s) of the top and/or bottom plates, said fluid holder having been inserted between the plates prior to closure of the device (e.g., said fluid holder having been placed within or on the recess or other area of the bottom or top plate prior to closure). In certain embodiments, the passageway defines a distinct channel between an inlet and an outlet of the fluid holder (e.g., pre-welded). In certain embodiments, the fluid passageway is only formed when the device is in a closed state, otherwise the fluid holder does not have a passageway defining a distinct channel between an inlet and an outlet of the fluid holder.

In some embodiments, the temperature forcing device is capable of both cooling and heating the fluid. In some embodiments, the temperature forcing device includes a solid state device (e.g., a Peltier device and/or a thermoelectric cooler). In some embodiments, the temperature forcing device includes a resistive heater. In some embodiments, the temperature forcing device includes a compressor. In some embodiments, the temperature forcing device may include at least one fin disposed in at least one of the bottom plate and/or the top plate.

In some embodiments, the system includes at least one latch disposed in or on at least one of the bottom plate and the top plate or in or on a support or housing for at least one of the bottom plate and the top plate.

In some embodiments, the system has at least one fluid holder mounted to a mounting sheet.

In some embodiments, the system has at least one fluid holder (e.g., and mounting sheet) shaped and sized to be inserted into the device and removed therefrom.

In some embodiments, the system includes at least one power supply electrically coupled to a resistive heater disposed within or upon or under at least one of the top plate and the bottom plate. In some embodiments, the system includes at least one power supply electrically coupled to a solid state device (e.g., a Peltier device and/or a thermoelectric cooler, e.g., a dry solid state device) disposed within or upon or under at least one of the top plate and the bottom plate.

In some embodiments, the system includes at least one pin protruding from the bottom plate and/or the top plate, wherein each of the at least one pins is inserted through a corresponding hole in the fluid holder and/or its mounting sheet to secure the fluid holder and/or its mounting sheet when positioned within the temperature forcing device.

In some embodiments, the system is free from any heat transfer fluid.

In some embodiments, the temperature forcing device has a maximum operating temperature (e.g., the maximum controlled temperature of the fluid) from about 40 degrees C. to about 60 degrees C., or from about 40 degrees C. to about 50 degrees C., or from about 40 degrees C. to about 45 degrees C. In some embodiments, the temperature forcing device has an operating temperature range (e.g., a range of controlled temperature of the fluid) that encompasses the range from about 1 degrees C. to about 60 degrees C., or from about 20 degrees C. to about 50 degrees C., or from about 30 degrees C. to about 45 degrees C.

In some embodiments, the system accommodates (e.g., permits) a maximum flow rate through the temperature forcing device of from about 5 L/min to about 15 L/min, or from about 7 L/min to about 13 L/min, or from about 9 L/min to about 12 L/min.

In some embodiments, the therapeutic fluid includes at least one of blood, crystalloid and dialysate.

In some embodiments, the heat transfer fluid is selected from the group consisting of water, saline, oil, silicone fluid, propylene glycol, and a combination thereof.

Also described herein is a flexible fluid holder for containing a fluid (e.g., a therapeutic fluid or a heat transfer fluid), said fluid holder including: a fluid inlet, allowing the fluid to flow into the fluid holder; a fluid outlet allowing the fluid to flow out of the fluid holder; and at least one fluid passageway in the fluid holder fluidly connecting the fluid inlet to the fluid outlet. In certain embodiments, the fluid passageway is defined by a top plate and/or a bottom plate of a solid-state device into which the fluid holder is inserted, said passageway formed upon closure of the top plate and bottom plate.

In some embodiments, the top plate and/or the bottom plate include at least one recession and/or at least one protrusion (e.g., for creating said passageway upon closure of the top plate and bottom plate, e.g., said top plate and bottom plate brought into proximity or touching along an edge upon closure).

In another embodiment, a fluid holder for containing a therapeutic fluid includes a fluid inlet, allowing the therapeutic fluid to flow into the fluid holder; a fluid outlet allowing the therapeutic fluid to flow out of the fluid holder; and at least one fluid passageway disposed within the fluid holder fluidly connecting the fluid inlet to the fluid outlet. The fluid passageway is defined by at least one protrusion and/or at least one recession in the interior walls of a solid-state device into which the fluid holder is inserted (e.g., said passageway formed when the device is in a closed state).

Also described herein is a method of adjusting the temperature of a fluid that includes: providing a temperature forcing device having a bottom plate and a top plate hingedly coupled to the bottom plate. At least one of the bottom plate and the top plate comprises an area (e.g., a recess) disposed therein or thereupon for receiving a flexible fluid holder (e.g., plastic bag) through which fluid to be heated and/or cooled will flow. The top plate and/or the bottom plate comprise(s) at least one recession and/or at least one protrusion for creating a fluid passageway between the top plate and the bottom plate upon closure of the temperature forcing device, said fluid passageway defining a channel between a fluid inlet and a fluid outlet of the flexible fluid holder. The top plate and/or the bottom plate may comprise a solid state device and/or a resistive heater and/or a heater exchanger from a compression cycle disposed therewithin, thereupon, or thereunder. The method further includes: inserting a fluid holder between the bottom plate and the top plate; positioning the top plate proximate the bottom plate (e.g., thereby forming a channel along which fluid may flow within the fluid holder from an inlet to an outlet, said channel formed due to ridges, grooves, and/or other textural features of the top plate and/or the bottom plate); delivering the fluid to a fluid inlet disposed in the fluid holder; and delivering power to at least one power supply electrically coupled to the temperature forcing device in order to adjust the temperature of the fluid as it flows from the fluid inlet to the fluid outlet of the flexible fluid holder between the top plate and the bottom plate of the temperature forcing device. The method may include implementing one or more features of the system embodiments described herein.

Throughout the description, where an apparatus, systems or compositions are described as having, including, or comprising specific components, or where methods are described as having, including, or comprising specific steps, it is contemplated that, additionally, there are systems or compositions of the present invention that consist essentially of, or consist of, the recited components, and that there are methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The following description is for illustration and exemplification of the disclosure only, and is not intended to limit the invention to the specific embodiments described.

The mention herein of any publication, for example, in the Background section, is not an admission that the publication serves as prior art with respect to any of the claims presented herein. The Background section is presented for purposes of clarity and is not meant as a description of prior art with respect to any claim.

BRIEF DESCRIPTION OF THE DRAWING

A full and enabling disclosure of the present disclosed embodiments, including the best mode thereof, directed to one of ordinary skill in the art, is set forth in the specification, which makes reference to the appended figures, in which.

DESCRIPTION OF THE INVENTION

Figure 1:
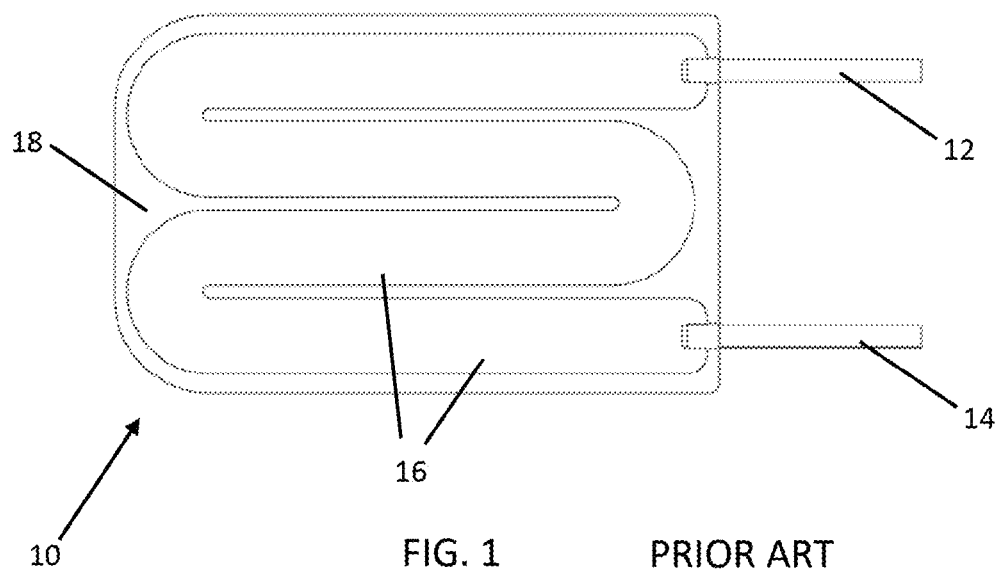
FIG. 1 illustrates an exemplary top view depiction of a disposable bag with an integral, welded-in serpentine fluid path.

Reference will now be made in detail to the present disclosed embodiments, one or more examples of which are illustrated in the accompanying drawings. The detailed description uses numerical and/or letter designations to refer to features in the drawings. Like or similar designations in the drawings and description have been used to refer to like or similar parts of the present embodiments.

Some embodiments of the present disclosure provides systems and methods for heating and cooling therapeutic fluids, utilizing a dry, solid-state heating and cooling device that does not employ a heat transfer fluid. The solid-state system of the present embodiments is "dry" because it does not use a heat transfer fluid (such as glycol, water, etc.) to transfer heat into and out of the therapeutic fluid. However, in other embodiments, systems and methods of the present disclosure may be used for heating and/or cooling heat transfer fluids. The system may include a hinge to ease the placement and removal of the bag. The system may also include a plurality of fins to aid in heat transfer. In addition, the system may include one or more latches to ensure the solid state heating and cooling device remains closed while in operation.

FIG. 1 illustrates a top view of an exemplary fluid holder 10 including a fluid inlet 12, a fluid outlet, 14, serpentine passages 16, and a mounting plate 18 to which the serpentine passages 16 are welded.

Figure 2:
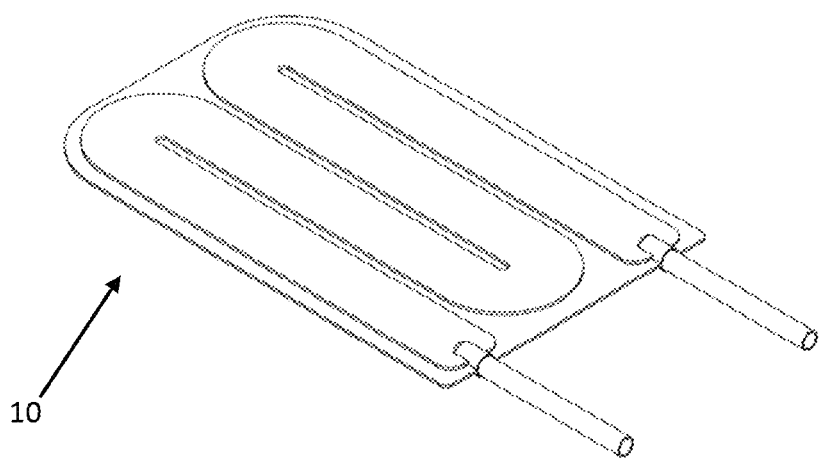
FIG. 2 illustrates an exemplary perspective view depiction of a disposable bag with an integral, welded-in serpentine fluid path.

FIG. 2 illustrates a perspective view of the exemplary fluid holder of FIG. 1. In both FIGS. 1 and 2, the fluid entering and exiting the fluid holder is a heat transfer fluid, not a therapeutic fluid such as blood and/or dialysate. The exemplary embodiments of FIGS. 1 and 2 would also include other heat exchangers (not shown) in order to transfer heat from the heat transfer fluid into the therapeutic fluid and/or temperature management device, or vice versa.

Figure 3:
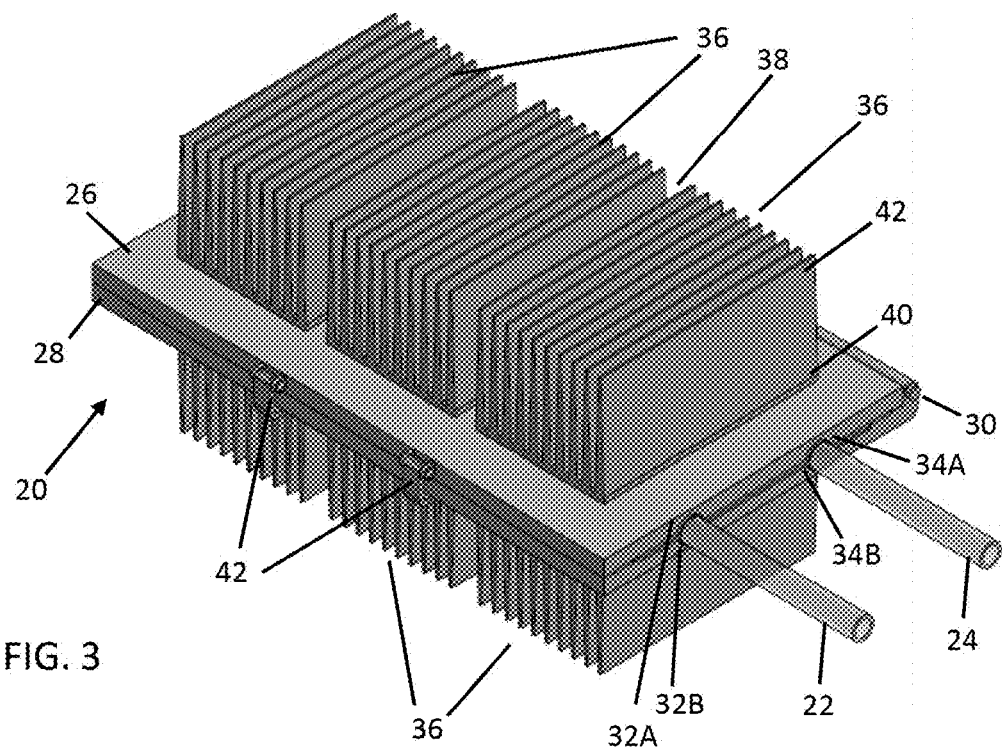
FIG. 3 illustrates a perspective view depiction of a solid-state dry temperature control system with a built-in integral fluid path and hinged opening in a closed configuration, according to an illustrative embodiment.

FIG. 3 illustrates a perspective view of a solid-state device 20 according to the present embodiments. In the depiction shown in FIG. 3, the solid-state device 20 is in a closed position. The solid-state device 20 may include a fluid inlet 22 for receiving a therapeutic fluid (such as blood or dialysate) from a patient and/or pump, as well as a fluid outlet 24, for delivering a heated and/or cooled fluid back to the patient. Each of the fluid inlet 22 and fluid outlet 24 are fluidly coupled to a fluid holder 44 (not shown) which in the embodiment of FIG. 3 is within the solid-state device 20. As such, each of the fluid inlet 22 and fluid outlet 24 are inserted into the solid-state device 20 when the fluid holder 44 (not shown) is inserted into the solid-state device 20. Each of the fluid inlet 22 and fluid outlet 24 may include cylindrical tubing that may be fluidly connected to other system tubing and/or components via various connection mechanisms (e.g., nipples, couplings, valves, elbows, unions, tees, male and female adaptors, compression fittings, face seal fittings, bard tubed fittings, quick disconnect fittings, and other suitable fluid coupling mechanisms). The solid-state device 20 may include a top plate 26 and a bottom plate 28, the top and bottom plates 26, 28 being hingedly coupled via one or more hinges 30. In some embodiments, the one or more hinges 30 will be proximate the fluid inlet 22 while in other embodiments the one or more hinges 30 will be proximate the fluid outlet 24. The one or more hinges 30 allow the top plate 26 to rotate open about the hinge 30 thereby providing space between the top plate 26 and the bottom plate 28 to allow the fluid holder 44 (not shown) to be inserted. In some embodiments, the one or more hinges 30 may be located at the opposite side of the fluid inlet 22 and the fluid outlet 24. In some embodiments, the solid-state device 20 further comprises a blood detector, fluid temperature sensors (e.g., resistive, infrared, fiber optic temperature sensor), a pressure transducer, patient temperature probes, an air detector (e.g., ultrasonic sensor detecting air in fluid), and/or a fluid flow rate detector.

Referring still to FIG. 3, the solid-state device 20 may include a top inlet recess 32A and a bottom inlet recess 32B which each may include contours and/or recesses disposed within each of the top plate 26 and the bottom plate 28 to allow the fluid inlet 22 to act as a fluid conduit through the top and bottom inlet recesses 32A, 32B while the solid-state device is in a closed position. Similarly, the solid-state device 20 may also include a top outlet recess 34A and a bottom outlet recess 34B which each may include contours and/or recesses disposed within each of the top plate 26 and the bottom plate 28 to allow the fluid outlet 24 to act as a fluid conduit through the top and bottom outlet recesses 34A, 34B while the solid-state device is in a closed position. The top inlet recess 32A and the bottom inlet recess 32B may each be disposed proximate the fluid inlet 22 to allow fluids to enter the solid-state device while the top outlet recess 34A and the bottom outlet recess 34B may each be disposed proximate the fluid outlet 24 to allow fluids to exit the solid-state device. The solid-state device 20 may also include one or more pluralities of fins 36 extending vertically upward from the top plate 26 and extending vertically downward from the bottom plate 28. One or more spaces 38 may separate pluralities of fins 36 from one another. Each fin may include a proximal portion 40 disposed close to the respective top plate 26 or bottom plate 28, as well as a distal portion 42 extending away from the respective top plate 26 or bottom plate 28. In some embodiments, each fin of the plurality of fins 36 may be thinner at the distal portion 42 than at the proximal portion 40. Stated otherwise, each proximal portion 40 may be thicker than each distal portion 42. In other embodiments, each fin of the plurality of fins 36 may have a uniform thickness from the proximal end 40 to the distal end 42.

Still referring to FIG. 3, the one or more plurality of fins 36 may be aligned widthwise (as shown in FIG. 3), lengthwise (not shown) or in hybrid configurations including one or more pluralities of fins 36 aligned in widthwise, lengthwise, diagonal and/or other configurations. The one or more pluralities of fins 36 may also be oriented such that they extend away from the top and bottom plates 26, 28 at an angle (i.e., the plain defined through the center of each fin intersects the plain defined by the top plate 26 and/or bottom plate 28 at an angle other than 90 degrees). The solid-state device 20 may include various numbers of pluralities of fins 36 on each of the top plate 26 and bottom plate 28, as well as various numbers of fins within each plurality of fins 36. For example, 3 pluralities of fins 36 each including 10 fins may be disposed within each of the top and bottom plates 26, 28. In other embodiments, from about 2 to about 4 pluralities of fins 36 each including from about 8 to about 12 fins may be disposed within each of the top and bottom plates 26, 28. In other embodiments, from about 1 to about 10 pluralities of fins 36 each including from about 1 to about 20 fins may be disposed within each of the top and bottom plates 26, 28. Other embodiments may include other numbers of pluralities of fins 36 as well as other numbers of fins within each plurality of fins 36. In some embodiments the top and bottom plates 26, 28 may have the same number and arrangement of pluralities of fins 36 while in other embodiments the top and bottom plates 26, 28 may have different numbers of pluralities of fins 36 and/or fin arrangements. The solid-state device 20 may include one or more latches 42 for ensuring that the top plate 26 stays coupled to the bottom plate 28 while the solid-state device 20 is in operation. The one or more latches 42 may be hingedly coupled to the top plate 26 and/or the bottom plate 28. Other suitable mechanisms of coupling the top and bottom plates 26, 28 together as well as for coupling the one or more latches 42 to the top and/or bottom plates 26, 28 are also possible.

Referring still to FIG. 3, the solid-state device 20 may be used for both heating and cooling. Each of the top plate 26 and bottom plate 28 may include one or more embedded resistance heaters (not shown) or one or more Peltier heater/coolers and may be electrically coupled to one or more power sources (not shown) in order to provide heating and/or cooling to the interior of the solid-state-device 20. For example, the temperature forcing device disposed within each of the top and bottom plates 26, 28 may be configured as Peltier devices (or Peltier heat pump) allowing each of the top and bottom plates 26, 28 to provide heating and/or cooling to the interior of the solid-state device, depending on which direction current is flowing through the Peltier device. Each Peltier device and/or other temperature forcing device may be used in connection with the one or more pluralities of fins 36 in use cases in which it is desirable to provide cooling to the interior of the solid-state device 20. In addition, the one or more pluralities of fins 36 may provide passive cooling to the interior of the solid-state device 20 since room temperature (usually between 55 degrees Fahrenheit and 85 degrees Fahrenheit) is often less than the normothermic temperature of about 98.6 degrees Fahrenheit (+/−2-3 degrees Fahrenheit). The geometry of the fins, the materials the fins are compose of, the number of fins, the groupings of fins, the spacing between fins and the orientations of the fins may be varied to enhance the heat transfer effectiveness of the solid-state device 20. The solid-state device 20 may provide cooling and/or heating to the therapeutic fluid without the need for a dedicated heat transfer fluid or any moving parts. In some embodiments, resistance heating elements and pluralities of fins 36 may be disposed within both the top and bottom plates 26, 28. In other embodiments, resistance heating elements and/or pluralities of fins 36 may be disposed in either the top plate 26 or bottom plate 28, but not both. The pluralities of fins 36 may be composed of a different material or materials than that of the top and bottom plates 26, 28 in order to enhance heat transfer. The solid-state device 20 may also include a fan (not shown) to increase the flow of air across the one or more pluralities of fins 36.

Figure 4:
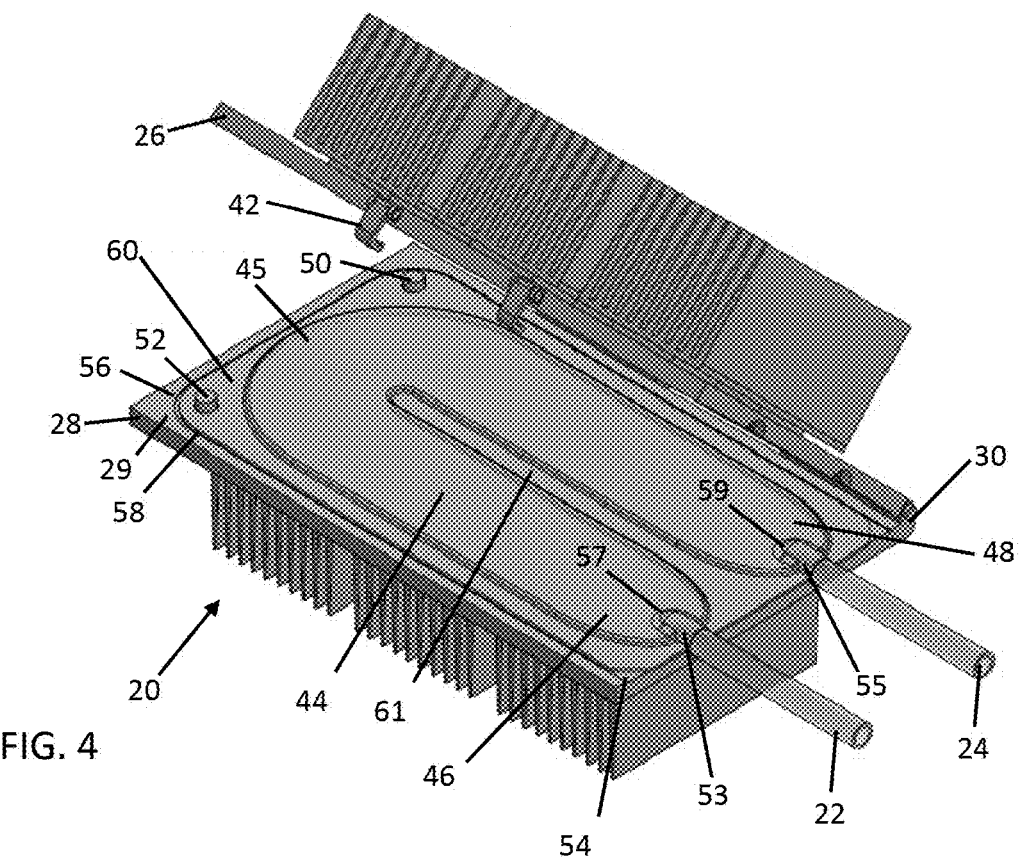
FIG. 4 illustrates a perspective view depiction of a solid-state dry temperature control system with a built-in integral fluid path and hinged opening in an open configuration, according to an illustrative embodiment.

FIG. 4 illustrates a perspective view of the solid-state device 20 in an open position with a fluid holder 44 placed within. In the embodiment of FIG. 4, the one or more latches 42 have been released and the top plate 26 has been rotated about the hinge 30 into an open position, allowing the fluid holder 44 to be placed within the solid-state device 20. The fluid holder 44 may include a first portion 46 proximate the fluid inlet 22 and a second portion 48 proximate the fluid outlet 24. Between the first portion 46 and the second portion 48, the fluid holder may include a rounded portion 45 at the opposite side of the solid-state device 20. The fluid holder 44 may include a mounting sheet 60 which helps to ensure both that the fluid holder 44 is positioned in precisely the correct location within the solid-state device 20, and also to ensure an even distribution of heat transfer from the solid-state device 20 into the fluid holder 44. The solid-state device may include first and second pins 50, 52 which may protrude upwardly from a top surface 29 of the bottom plate 28 through openings in the mounting sheet 60 to ensure the fluid holder 44 is accurately positioned within the solid-state device 20.

FIG. 4 further illustrates an inlet coupling 53 circumferentially disposed around one end of the fluid inlet 22 as well as an outlet coupling 55 circumferentially disposed around a fluid outlet 24. Each of the inlet coupling 53 and the outlet coupling 55 form the respective transitions between the interior of the fluid holder 44 and the fluid inlet 22 and/or fluid outlet 24. The inlet coupling 53 and the outlet coupling 55 may each include a diameter that is slightly greater than the fluid inlet 22 and outlet 24 such that the fluid inlet 22 and outlet 24 may be rigidly inserted into the inlet coupling 53 and the outlet coupling 55 via a compression fit and/or other mechanisms (epoxy, adhesion, sintering, adjustable hose clamp and/or ring clamp). The inlet and outlet couplings 53, 55 may be composed of a material that is harder and/or more rigid than the fluid inlet 22 and fluid outlet 24 (as well as any associated tubing to which the fluid inlet and outlet 22, 24 are connected) such that the inlet and outlet couplings 53, 55 help to support the weight of the top plate 26 (and any compression associated with the latches 42 when the solid-state device is closed). For example, as the top plate 26 comes to rest on top of the bottom plate 28, the recessed portions 32A, 34A of the top plate 26 will come in contact with and/or interface with the inlet and outlet couplings 53, 55, thereby allowing the weight and/or downward force of the top plate to be distributed across the inlet and outlet couplings 53, 55 (as well as the first and second pins 50, 52.) The height of the first and second pins 50, 52 (as well as the diameters of the inlet and outlet couplings 53, 55) may be designed such that the spacing between the top and bottom plates 26, 28 is optimal from an operational point of view when the solid-state device 20 is in a closed position. For example, if the top and bottom plates 26, 28 are squeezed together too tightly, damage may occur to the fluid holder 44 and flow through the fluid holder 44 may be restricted. If the top and bottom plates 26, 28 are not brought closely enough together, heat transfer into and out of the fluid holder 44 may be hindered. The first and second pins 50, 52 and the inlet and outlet couplings 53, 55 also ensure that the mounting sheet 60 and fluid holder 44 mounted thereon cannot be disposed within the solid-state device 20 in an incorrect orientation.

Still referring to FIG. 4, the fluid holder 44 may include an inlet tapered portion 57 and an outlet tapered portion 59, each coupling the fluid holder 44 to the respective inlet and outlet couplings 53, 55. Each of the inlet and outlet tapered portions 57, 59 also provide gradual transitions between the inlet and outlet couplings 53, 55 and the fluid holder 44, allowing the fluid holder 44 to expand as needed while still remaining tightly coupled to the inlet and outlet couplings 53, 55. The inlet and outlet tapered portions 57, 59 help to increase the surface area around the inlet and outlet couplings 53, 55 to which the fluid holder 44 may be connected, thereby allowing for a more robust attachment. The fluid holder 44 may be attached to the inlet and outlet couplings 53, 55 (i.e., at the inlet and outlet tapered portions 57, 59) via epoxy, adhesion, glue, sintering, fusion, compression fit, tape and/or other suitable mechanisms. The connections and/or attachments between the fluid inlet and outlet 22, 24 and the inlet and outlet couplings 53, 55, as well as between the inlet and outlet couplings 53, 55 and the fluid holder 44 need to be robust enough so that upon removal from the steady state device 20, the fluid holder 44 doesn't become detached from the fluid inlet and/or fluid outlet 22, 24, even if the fluid holder 44 is suspended from the fluid inlet and outlet 22, 24 and filled with fluid.

Referring still to FIG. 4, the mounting sheet 60 may include angled and/or tapered corners 54 at the end proximate the fluid inlet and outlet 22, 24, which may aid in the insertion and/or removal of the fluid holder 44 within the solid-state device. The mounting sheet 60 may also include rounded corners 56 at the end opposite the fluid inlet and outlet 22, 24. The bottom plate 28 may include a first recessed portion 58 matching the general shape and thickness of the mounting sheet 60 such that the mounting sheet 60 is easily received within the bottom plate 28. In operation, (i.e., while the solid-state device 20 is in the closed position illustrated in FIG. 3) therapeutic fluid may flow into the fluid holder 44 at the first portion 46 via the fluid inlet 22, around the rounded portion 45, toward the second portion 48, and out through the fluid outlet 24. Thus, fluid inlet 22 is fluidly coupled to the fluid outlet 24 via the fluid holder 44.

Still referring to FIG. 4, each of the first portion 46, the second portion 48 and the rounded portion 45 are formed in the fluid holder 44 via corresponding recesses and protrusions in the top plate 26. The top plate 26 includes recesses and protrusions (not shown) that define the fluid passageways in the fluid holder 44 that form when the fluid holder 44 begins to fill, on account of fluid flowing therethrough. Stated otherwise, the fluid holder 44 itself does not include any fluid passageways prior to insertion into the solid-state device 20. The passageways (i.e., the first portion 46, the second portion 48 and the rounded portion 45) are formed in the fluid holder 44 as a result of the fluid holder 44 flexing around and conforming to the protrusions and recesses in the top plate 26 (and bottom plate 28) when the solid-state device 20 is closed and therapeutic fluid is flowing through the fluid holder 44. Recesses and protrusions that define the fluid passageways in the fluid holder 44 may be disposed within both the top plate 26 and/or the bottom plate 28. FIG. 4 also illustrates a passageway center-wall 61 which acts as a barrier defining the boundary between the passage way first portion 46 and the second portion 48. Therapeutic fluid may flow around the passageway center-wall 61 when the solid-state device 20 is in operation. The passageway center-wall 61 is formed in the fluid holder 61 as a result of a corresponding protrusion (not shown) in the top plate 26 (the protrusion in the top plate 26 being surrounded by recesses in the top plate 26 (and similarly on the bottom plate 28) that define the fluid passageways within the fluid holder 44.

Figure 5:
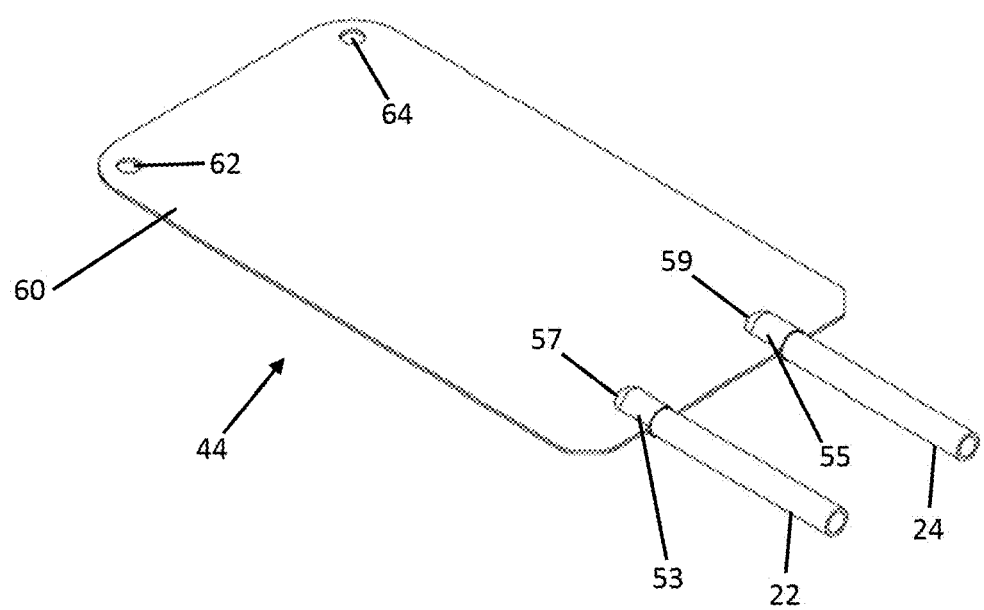
FIG. 5 depicts an empty fluid holder that may be used with the solid-state dry temperature control system of FIGS. 3 and 4, according to an illustrative embodiment.
Figure 6:
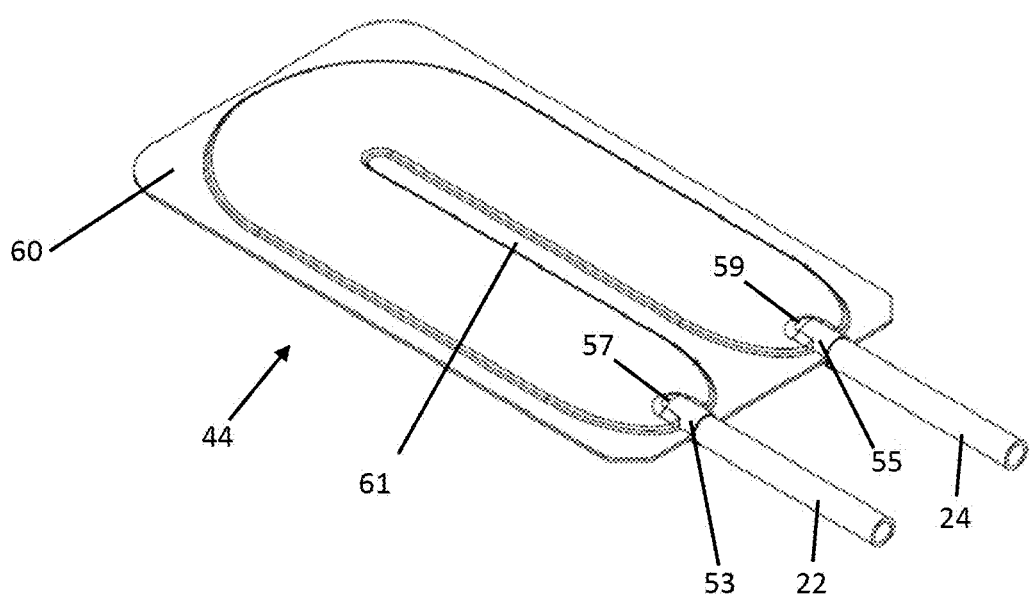
FIG. 6 depicts a full fluid holder that may be used with the solid-state device described herein.

FIG. 5 illustrates a perspective view of an empty fluid holder 44 with a first hole 64 disposed therethrough (through which the first pin 50 may be inserted) as well as a second hole 62 disposed therethrough (through which the second pin 52 may be inserted). In comparison to FIG. 4 (and also FIG. 6), the fluid holder 44 of FIG. 5 is empty whereas the fluid holders 44 FIGS. 4 and 6 are full. In the embodiment of FIG. 5, the fluid inlet 22 and fluid outlet 24 are disposed within the inlet and outlet couplings 53, 55, which are connected to the fluid holder 44 via the inlet and outlet tapered portions 57, 59. In the embodiment of FIG. 5, the mounting sheet 60 appears integral to (and monolithic with) the fluid holder 44. Stated otherwise, in some embodiments, the mounting sheet 60 is a continuous portion of the fluid holder 44 that does not end up forming (or becoming a part of) the fluid passageways that form once the fluid holder 44 is placed in service within the solid-state device 20 (e.g., and the device is closed).

Referring still to FIG. 5, in other embodiments, the mounting sheet 60 (i.e., the portion of the fluid holder 44 at the edges and/or periphery of the fluid holder 44) may have different material properties than the center portion of the fluid holder 44 such that the mounting sheet 60 is less flexible than the center portion of the fluid holder 44, thereby making the fluid holder 44 easier to handle, more resistant to damage, and easier to insert within the solid-state device 20. In other embodiments, the interior of the fluid holder 44 may be formed by two sheets of material (for example, polymer and/or thermoplastic material, among other possible materials) that are joined via a seam that extends around the periphery of the fluid holder 44. In this embodiment, the seam that extends around the periphery of the fluid holder 44 would include the first and second holes 62, 64 disposed therethrough, and would allow for easy handling and insertion of the fluid holder 44 into the solid-state device 20, as described above. The seam that extends around the periphery of the fluid holder 44 may be formed via any suitable mechanisms for attaching the two sheets including (but not limited to) adhesion, glue, epoxy, sintering and/or fusing. The fluid holder 44 and the connections between the fluid holder 44 and the fluid inlet and outlet 22, 24 may be constructed (and/or or composed of suitable materials) such that the fluid holder 44 remains airtight and aseptic at all times during operation, and also to ensure the fluid holder 44 does not get torn, ripped or punctured when in use and/or during insertion or removal into and out of the solid-state device 20.

FIG. 6 illustrates a perspective view of a full fluid holder 44, as it would appear with therapeutic fluid disposed therein, with the portions around the periphery of the fluid holder 44 (i.e., the mounting sheet portion) not filled with therapeutic fluid due to the protrusions within the top and bottom plates 26, 28 not allowing the fluid holder 44 to expand in those areas. As discussed above, the fluid passageway that is formed within the fluid holder 44 around the passageway center-wall 61 is defined by the recesses and protrusions in the top plate 26 and bottom plate 28 (in certain embodiments, recesses and/or protrusions may be present in one or both of the top plate and bottom plate). A bottom perspective view (i.e., similar to the top perspective view of FIG. 6) would accordingly illustrate a similar fluid passageway defined in the underside of the fluid holder 44. The fluid holder 44, along with the inlet and outlet couplings 53, 55 as well as the fluid inlet and outlet 22, 24 disposed therein may be preassembled and/or prefabricated such that each time the solid-state device 20 is used, a new preassembled fluid holder 44 can be placed within the solid-state device 20, then disposed of afterward thereby eliminating the need to clean and/or sanitize either the solid-state device 20 or the fluid holder 44 (and mounting sheet 60). In the event that the solid-state device 20 requires cleaning or sterilization, the interior of the solid-state device can be easily accessed by positioning the solid-state device 20 into the open configuration depicted in FIG. 4 (and FIG. 7). The fluid holder 44 may be mounted on the mounting sheet 60 using any suitable means including adhesion (e.g., epoxy), compression fit, and other suitable means. In addition, the fluid holder 44 and mounting sheet 60 may be integrally formed and/or fabricated during the same continuous build or fabrication process such that the fluid holder 44 and mounting sheet 60 form a single, integral, monolithic structure.

Figure 7:
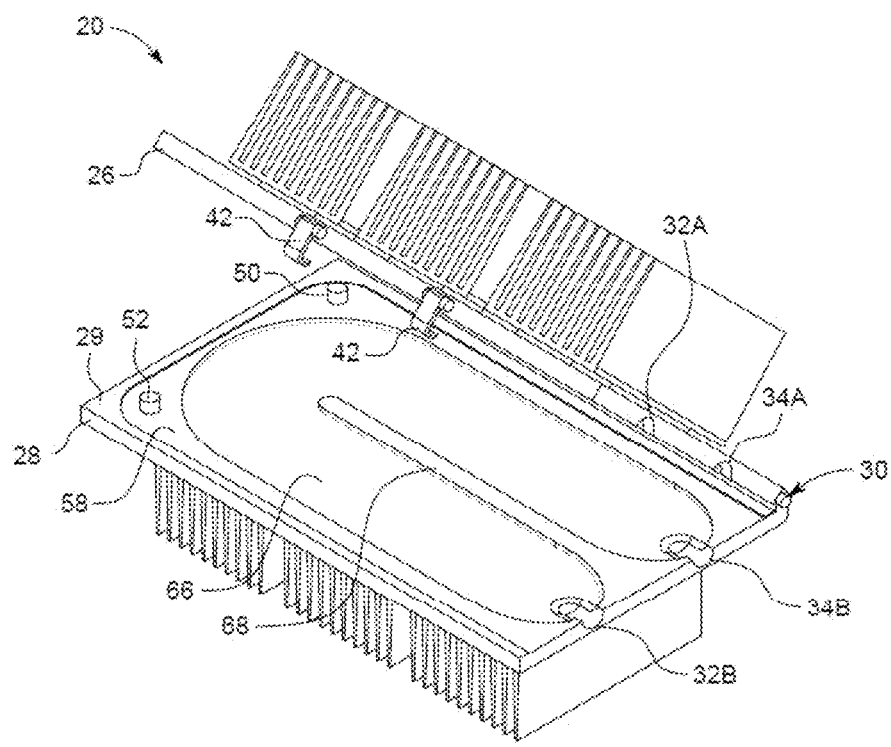
FIG. 7 illustrates a perspective view depiction of a solid-state dry temperature control system with a built-in integral fluid path and hinged opening in an open configuration, according to an illustrative embodiment.

FIG. 7 illustrates a perspective view of the solid-state device 20 without a fluid holder installed in it. The solid-state device 20 includes a top plate 26, hingedly connected via one or more hinges 30 to the bottom plate 28. Latches 44 keep the top plate 26 close to the bottom plate 28 when the solid-state device 20 is in a closed position. As discussed above, the top and bottom plates 26, 28 include top and bottom inlet and outlet recesses 32A, 32B, 34A, 34B to allow the fluid inlet and outlet 22, 24 to act as fluid conduits into and out of the solid-state device 20. First and second pins 50, 52 (also as discussed above) protrude upwardly from the top surface 29 of the bottom plate 28.

Still referring to FIG. 7, the solid-state device 20 may include bottom plate recess 66 and a bottom plate protrusion 68 disposed within the first recessed portion 58 of the bottom plate 28. The first recessed portion 58 is recessed slightly from the top surface 29 of the bottom plate 28 to allow for the thickness of the mounting plate 60 and/or unfilled portions of the fluid holder 44. The bottom plate recess 66 is further recessed (i.e., from both the top surface 29 of the bottom plate 28 as well as from the first recessed portion 58) to allow the fluid holder 44 to expand when it is inserted into the solid-state device 20 and filled with therapeutic fluids, thereby defining the outer boundaries of the fluid passageways within the fluid holder 44. A bottom plate protrusion 68 extends upwardly from the bottom plate recession 66, thereby defining the passageway center-wall 61 (shown in FIGS. 4 and 6) in the fluid holder 44 when the bag is in service within the solid-state device 20.

Figure 8:
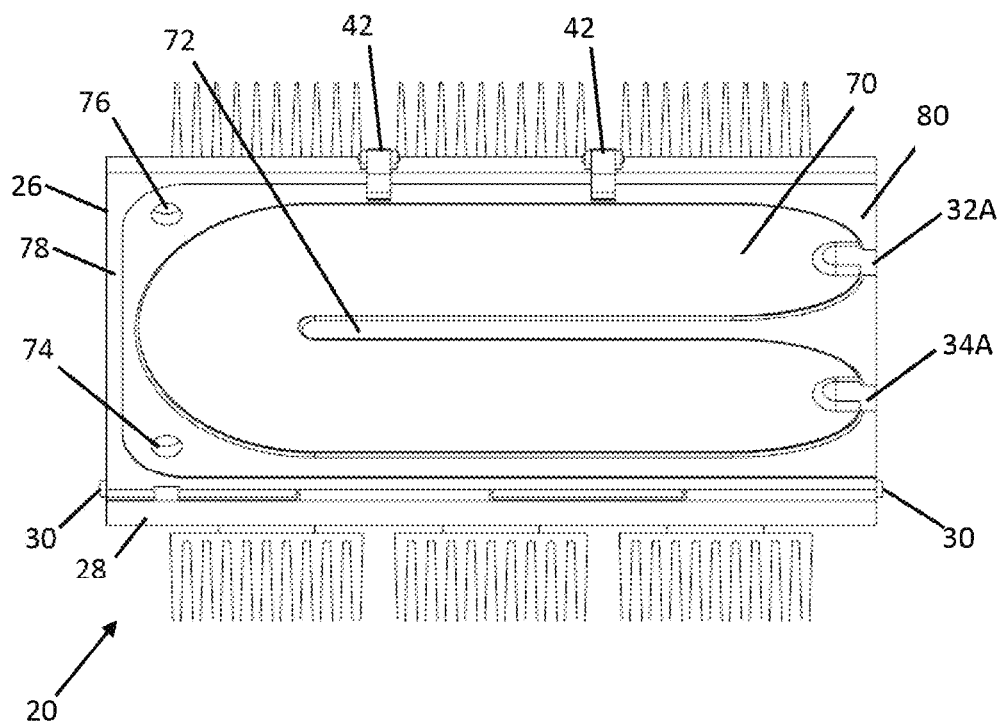
FIG. 8 illustrates a front view of a solid-state dry temperature control system with a built-in integral fluid path and hinged opening in an open configuration, according to an illustrative embodiment.

FIG. 8 illustrates a side view of the solid-state device 20 with the top plate 26 partially open and rotated about the one or more hinges 30. FIG. 8 illustrates the top inlet and outlet recesses 32A, 34A disposed within the top plate 26, as well as the latches 42 coupled to the top plate 26. In the embodiment of FIG. 8, a second recessed portion 80 is recessed slightly from a bottom surface 78 of the top plate 26 to allow for the thickness of the mounting plate 60 and/or unfilled portions of the fluid holder 44 (i.e., when the fluid holder 44 is inserted in the solid-state device 20). A top plate recess 70 is further recessed (i.e., from both the bottom surface 78 of the top plate 26 as well as from the second recessed portion 80) to allow the fluid holder 44 to expand when it is inserted into the solid-state device 20 and filled with therapeutic fluids, thereby defining the outer boundaries of the fluid passageways within the fluid holder 44. A top plate protrusion 72 extends downwardly from the top plate recession 70, thereby defining the passageway center-wall 61 (shown in FIGS. 4 and 6) in the fluid holder 44 when the bag is in service within the solid-state device 20. FIG. 8 also illustrates first and second pin holes 74, 76 disposed within the second recess portion 80 for receiving the first and second pins 50, 52 when the solid-state device 20 is closed.

Figure 9:
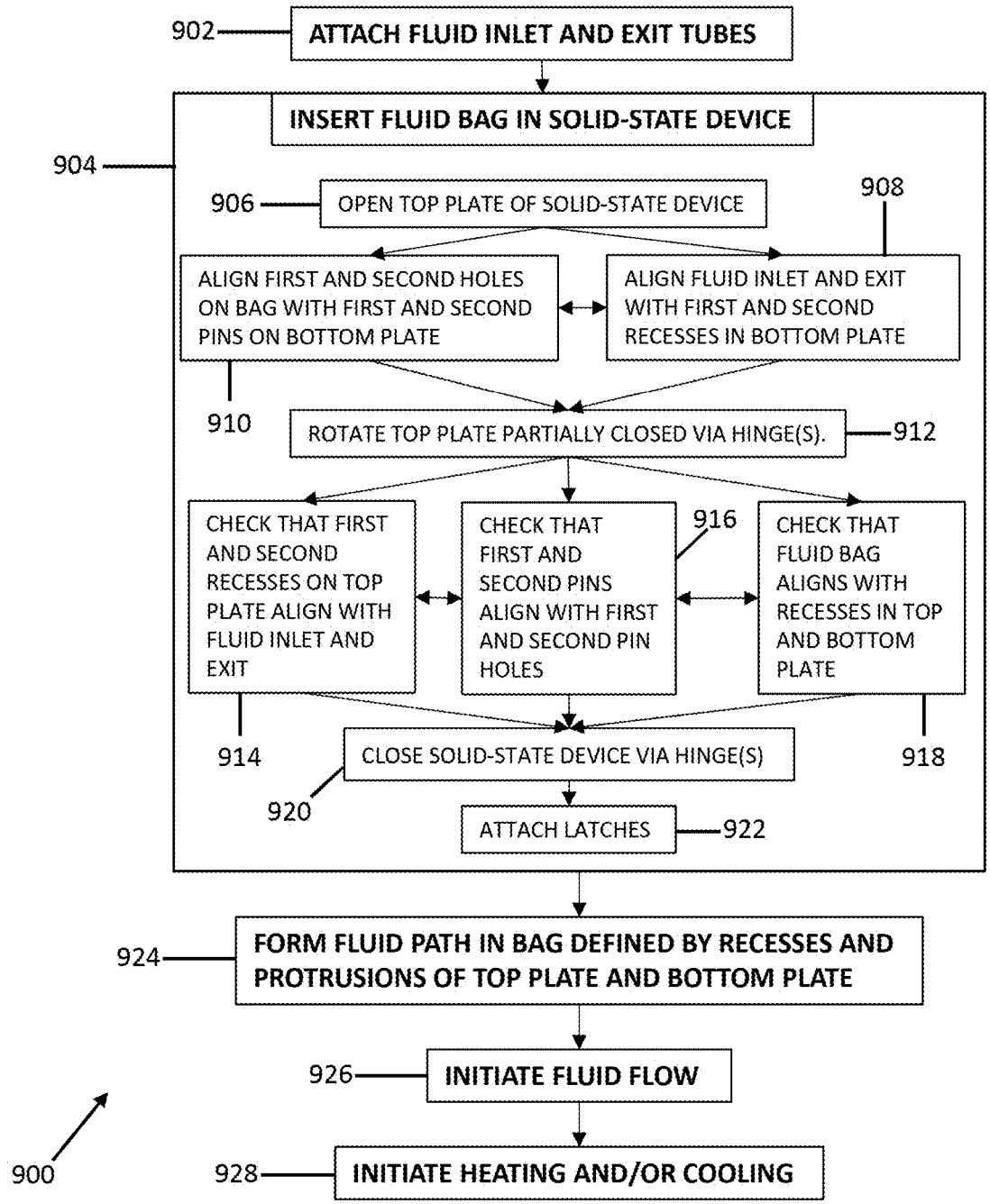
FIG. 9 illustrates a flow chart representation of a method of heating and/or cooling therapeutic fluid using the solid-state device, in accordance with aspects of the present disclosed embodiments.

FIG. 9 illustrates a method 900 of heating and/or cooling a therapeutic fluid according to the present claimed embodiments. At step 902, the method may include attaching fluid inlet and outlet tubes (not shown) to the fluid inlet and outlet 22, 24. Step 902 allows the fluid holder 44 to be fluidly coupled to a patient, dialysis system, blood warming system and/or other equivalent system. At step 904, the method 900 may include inserting the fluid holder 44 into the solid-state device 20. At step 924, the method 900 may include forming fluid passageways in the fluid holder 44 that are defined by recesses, contours, and protrusions disposed within the top and bottom plates 26, 28 (e.g., forming said fluid passageways by closing the device, i.e., bringing the top and bottom plates together). At step 926, the method 900 may include initiating a flow of therapeutic fluid (such as blood or dialysate) through the fluid inlet 22, fluid holder 44, and fluid outlet 24. At step 928, the method 900 may include initiating heating and/or cooling within the top and bottom plates 26, 28 via one or more temperature forcing device disposed therein, in order to adjust the temperature of the therapeutic fluid flowing through the solid-state device 20. The method 900 may include other steps and may skip steps detailed above. In addition, steps may be performed in a different order than what is illustrated in FIG. 9. Additional steps may include stopping the flow of therapeutic fluid through the solid-state device 20, discontinuing the heating and/or cooling within the solid-state device 20, opening the solid-state device 20, removing the fluid holder 44, removing the tubing from the fluid holder 44, and disposing of the fluid holder 44. In addition, the method 900 may include several sub-steps to step 904 (inserting the fluid holder 44 into the solid-state device) as detailed below.

Referring still to FIG. 9, the method may include several sub-steps that ensure that the fluid holder 44 is installed correctly into the solid-state device 20. Several of these sub-steps may not need to be performed in many cases. According to method 900, these sub-steps may include: at step 906 opening the top plate of the solid-state device 20; at step 908 aligning the fluid inlet and outlets 22, 24 with the first and second recess 32B, 34B in the bottom plate 28; at step 910 aligning the first and second holes 62, 64 in the fluid holder 44 with the first and second pins 50, 52 on the bottom plate 26; at step 912 rotating the top plate 26 partially closed via the one or more hinges 30; at step 914 checking that the first and second recesses 32A, 34A on the top plate 26 align with the fluid inlet and outlet 22, 24; at step 916 checking that the first and second pins 50, 52 align with the first and second pin holes 74, 76 on the top plate 26; at step 918, checking that the fluid holder 44 aligns with the recesses 58, 80 in the top and bottom plates 26, 28; at step 920 closing the solid-state device 20; and at step 922, attaching the one or more latches 42. Several of the steps illustrated in FIG. 9 may be optional, skipped, and/or performed in a different order than what is illustrated in FIG. 9.

The solid-state device 20 of the present embodiments eliminates the need for a dedicated heat transfer fluid. The solid-state device 20 of the present embodiments heats and cools the therapeutic fluids directly or indirectly, thereby reducing and/or eliminating the risk of infection attributed to the heat transfer fluid. In operation, the solid-state device 20 may include a maximum operating temperature from about 40 degrees C. to about 60 degrees C., or from about 40 degrees C. to about 50 degrees C., or from about 40 degrees C. to about 45 degrees C. In operation, the solid-state device 20 may accommodate a maximum flow rate of about 5 L/min (i.e., liters per minute) to about 15 L/min, or from about 7 L/min to about 13 L/min, or from about 9 L/min to about 12 L/min, or from about 10 L/min to about 11 L/min. One source of nosocomial pathogens in existing patient treatment devices is the heat transfer fluid, which has been eliminated from some embodiments of the system described in the present disclosure. In addition, the present embodiments allow for the use of fluid holders 44 that do not have predefined fluid passageways or channels within them. By allowing the fluid passageways to be defined in the fluid holder 44 via the recesses, protrusions and contours 58, 66, 68, 72, 78, 80 in the top and bottom plates 26, 28, a much simpler and easier to manufacture fluid holder 44 may be employed. The hinge 30 connecting the top and bottom plates 26, 28 makes inserting and removing the fluid holder 44 into and out of the solid-state device 20 quick and easy, while also providing convenient access to the interior of the solid-state 20 device for cleaning and sterilizing operations.

Figure 10:
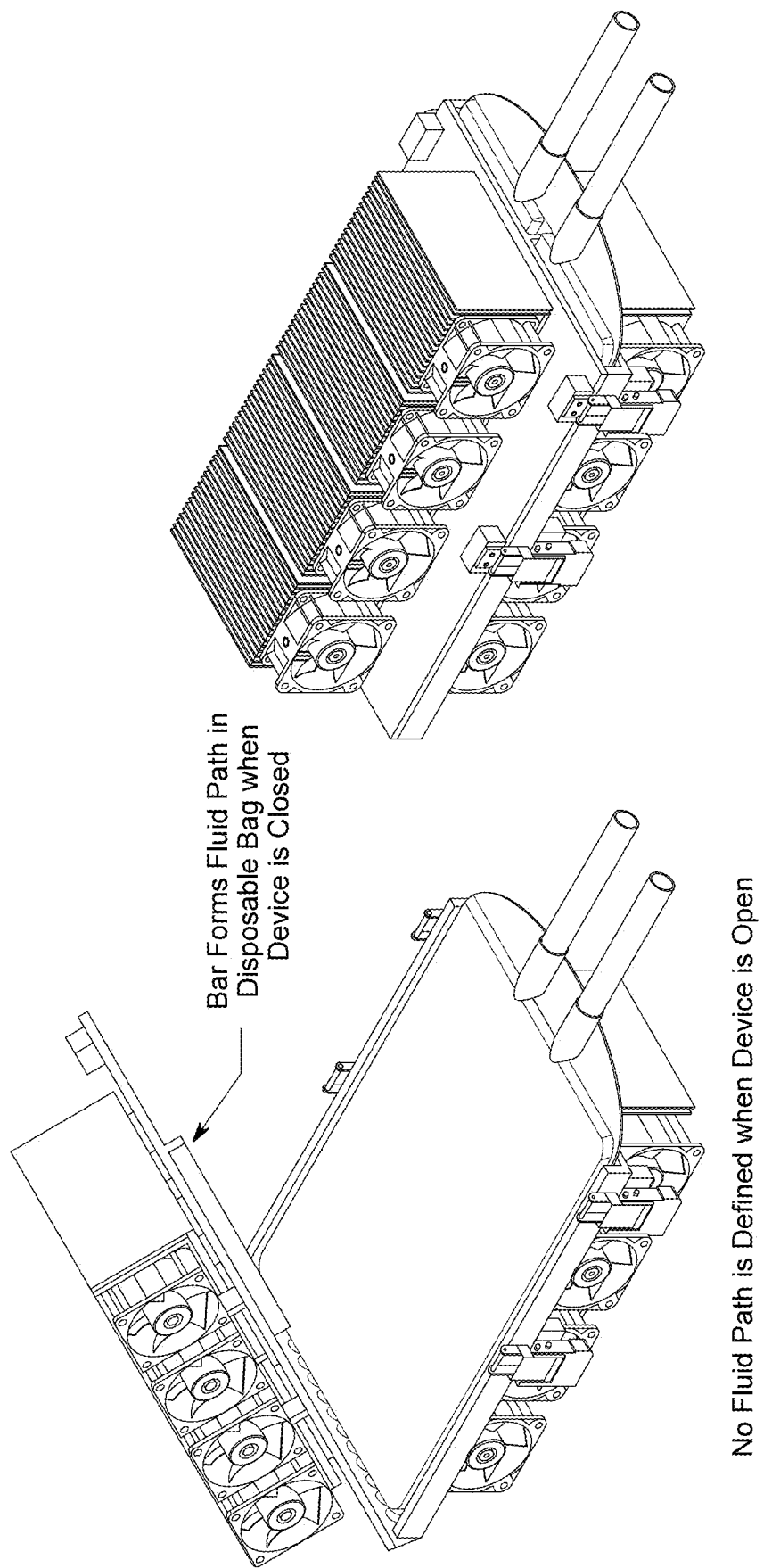
FIG. 10 illustrates a temperature forcing device in a system for heating and/or cooling a fluid, according to an illustrative embodiment.

FIG. 10 illustrates a temperature forcing device in a system for heating and/or cooling a fluid, according to a illustrative embodiment. A bar disposed in the top plate of the temperature forcing device forms a fluid path in a disposable bag placed in the device when the device is closed. There is no fluid path defined when the device is open. In this embodiment, thermoelectric Peltier heater/cooler components are depicted on both the top and bottom plates of the temperature forcing device.

Figure 11:
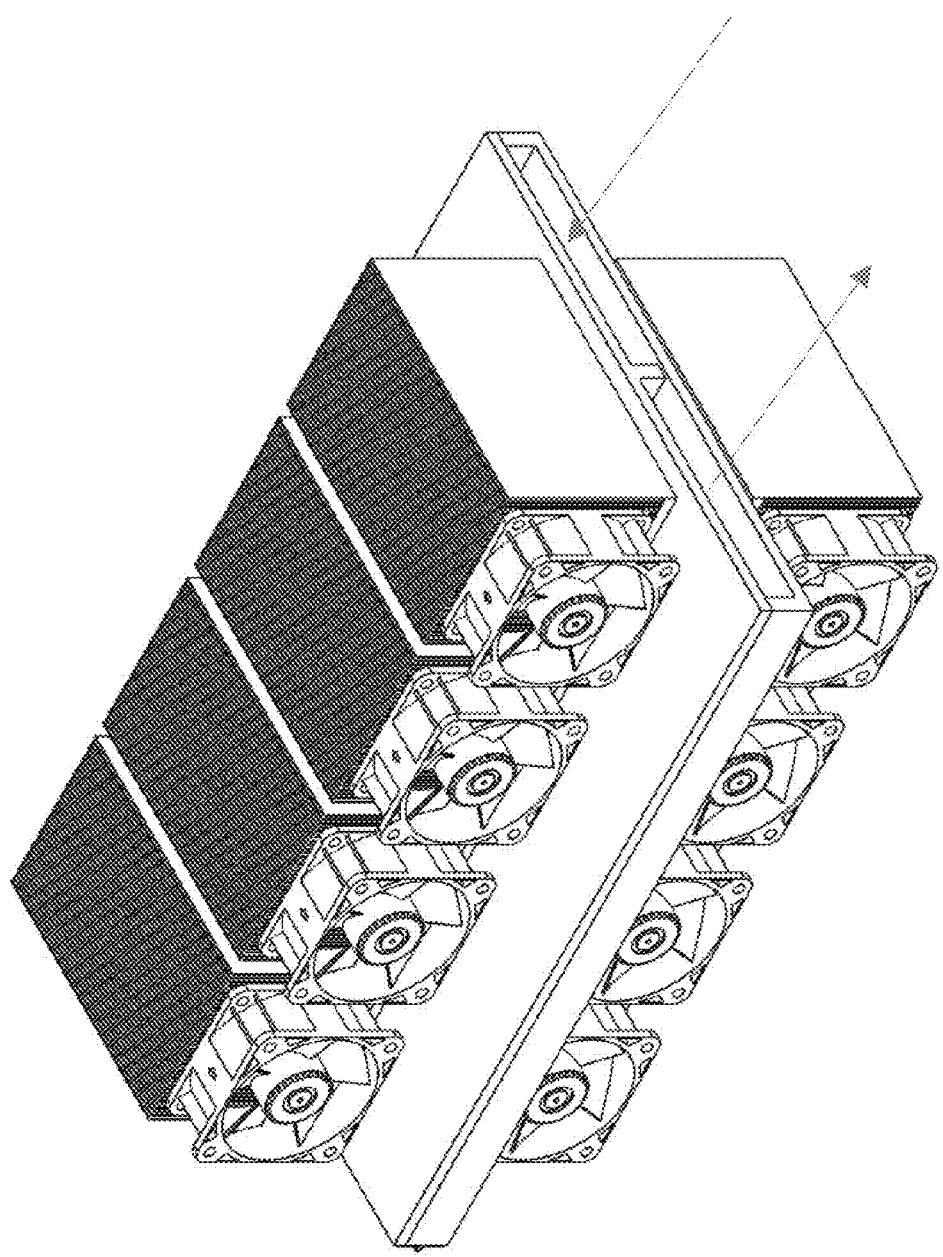
FIG. 11 illustrates a view of the temperature forcing device of FIG. 10 showing the inlet and outlet of the fluid path formed when the top and bottom plates are closed, according to an illustrative embodiment.

FIG. 11 illustrates a view of the temperature forcing device of FIG. 10 showing the inlet and outlet of the fluid path formed when the top and bottom plates are closed, with arrows illustrating direction of flow into the channel formed.

Figure 12:
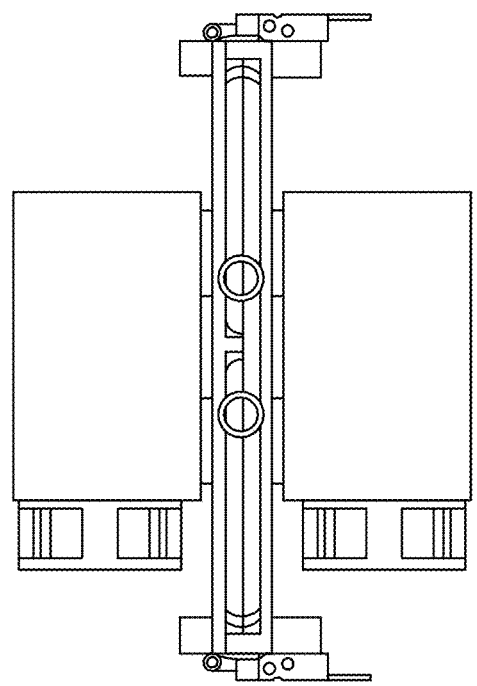
FIG. 12 illustrates a front view of the temperature forcing device of FIG. 10, according to an illustrative embodiment.
Figure 12:
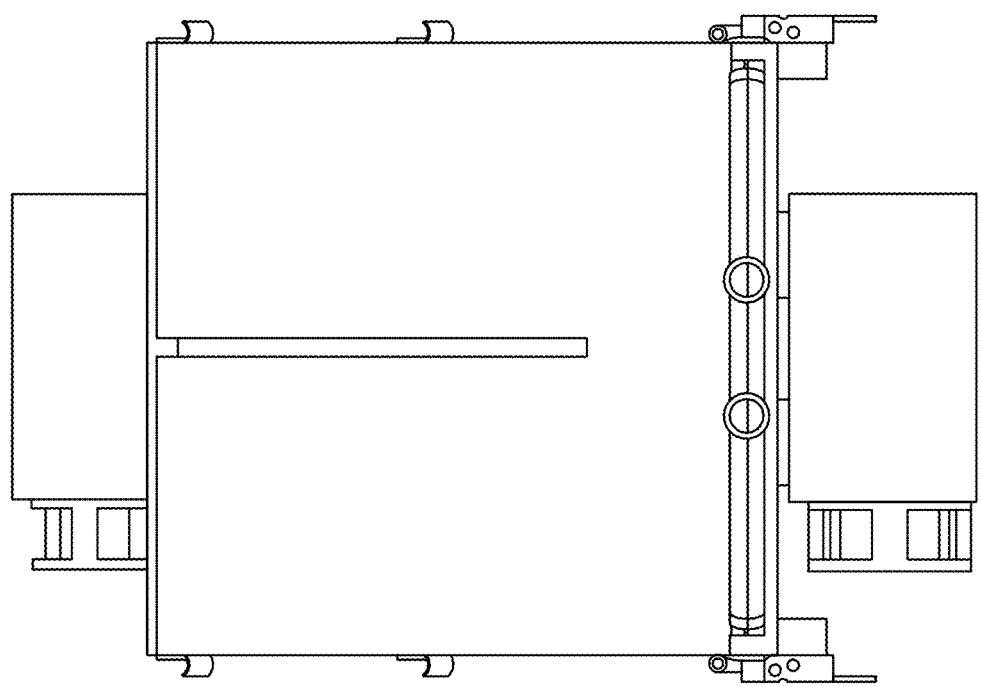
Figure 13:
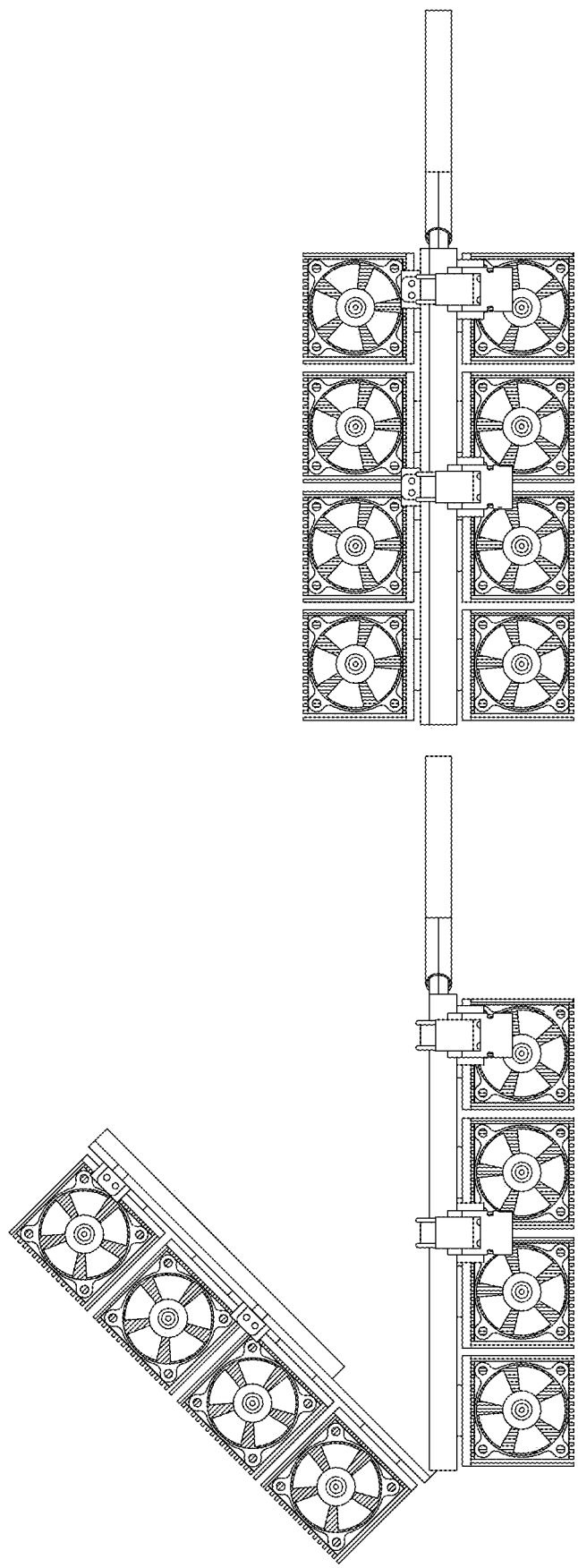
FIG. 13 illustrates a side view of the temperature forcing device of FIG. 10, according to an illustrative embodiment.
Figure 14:
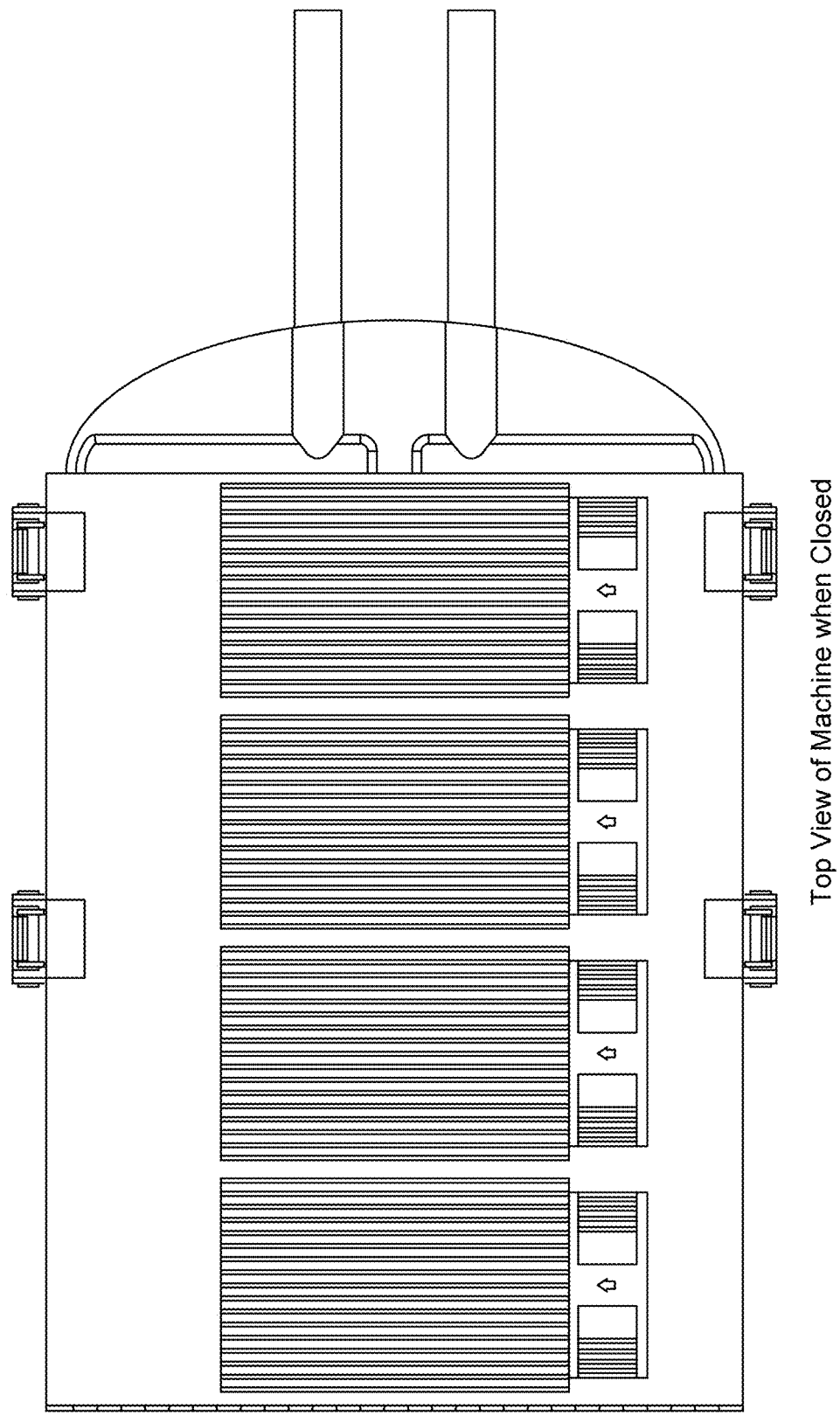
FIG. 14 illustrates a top view of the temperature forcing device of FIG. 10 when the device is closed, according to an illustrative embodiment.

FIGS. 12, 13, and 14 illustrates front, side, and top views of the temperature forcing device of FIG. 10, respectively.

Figure 15:
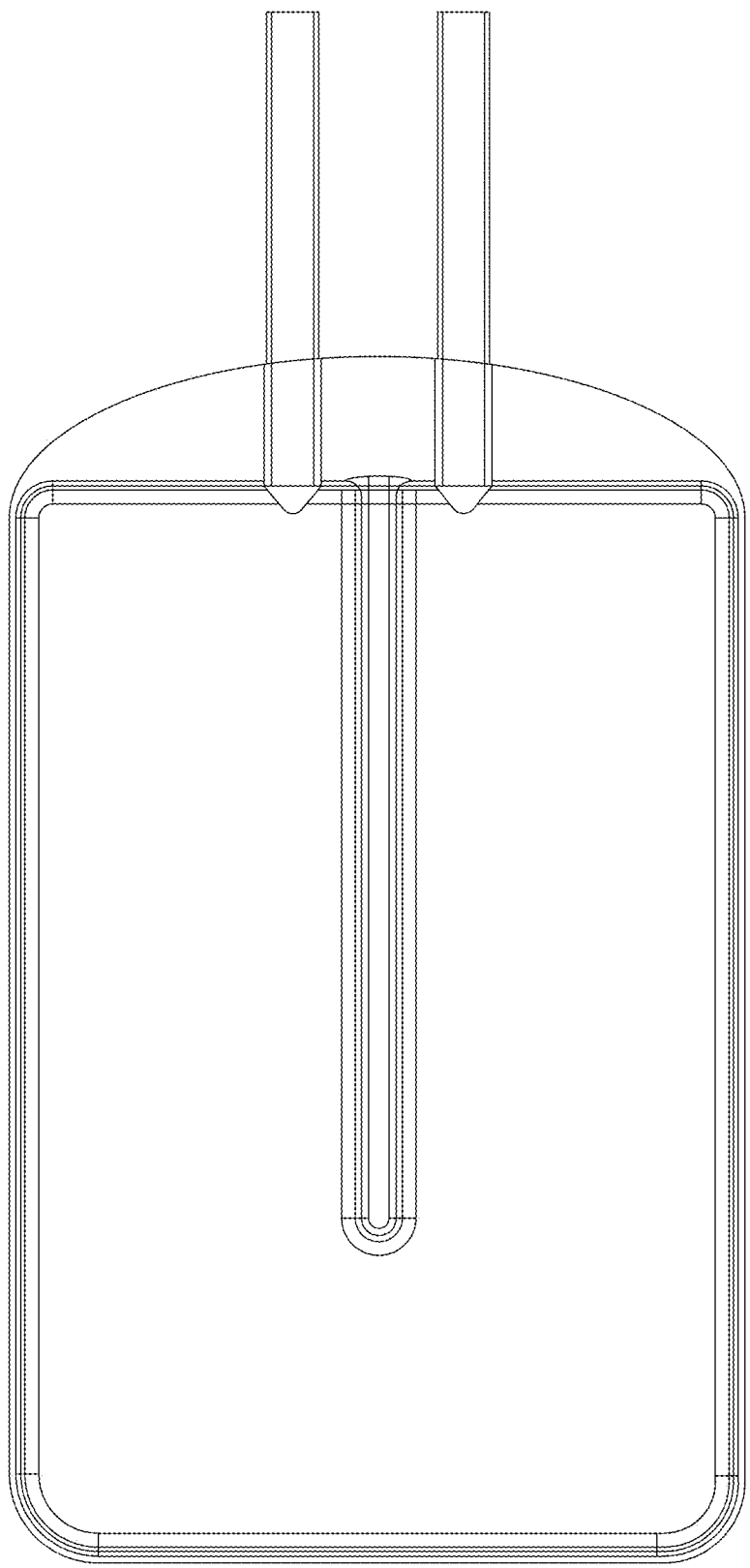
FIG. 15 illustrates a flexible fluid holder (disposable bag) with a fluid path formed by the temperature forcing device of FIG. 10 when the device is closed, according to an illustrative embodiment.
Figure 16:
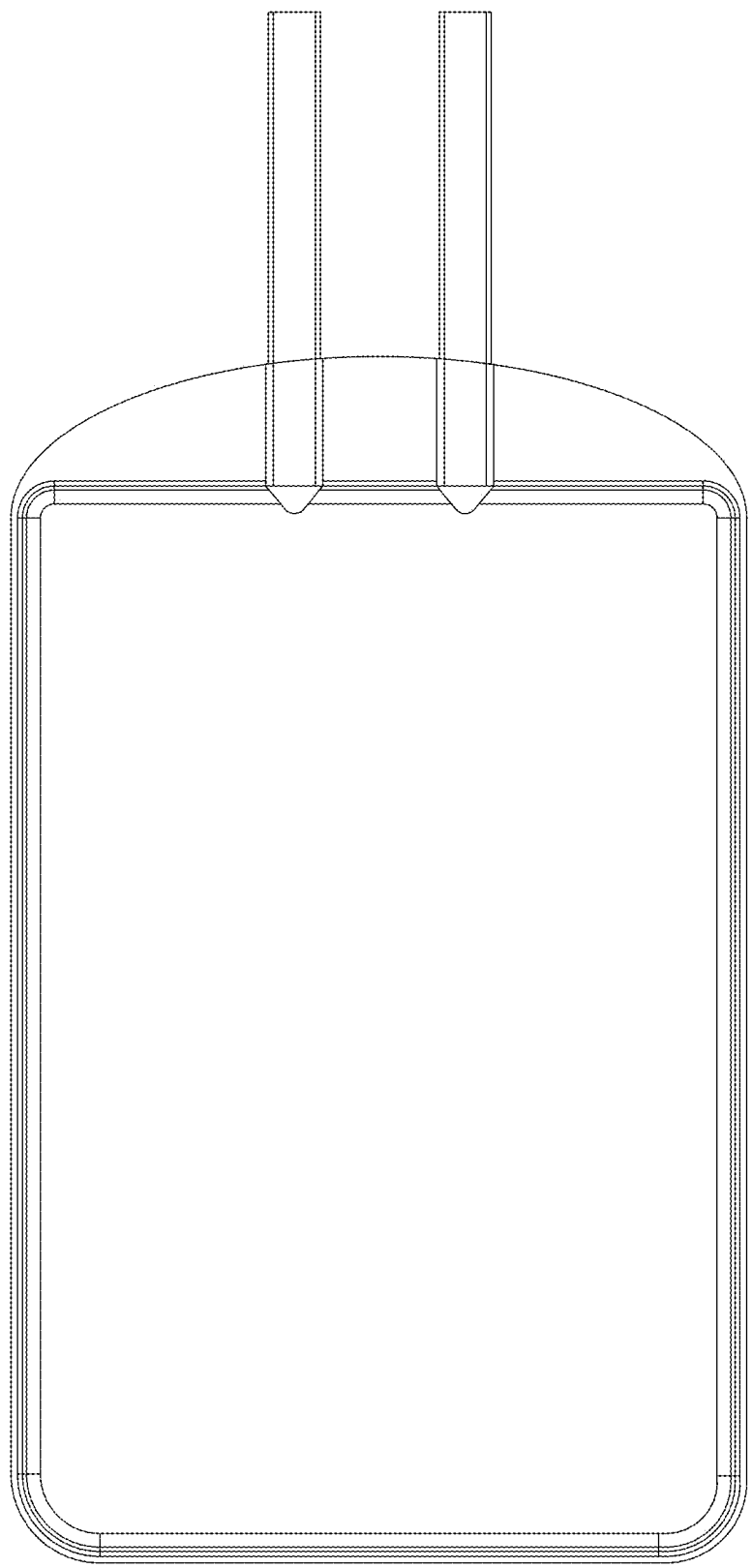
FIG. 16 illustrates a flexible fluid holder (disposable bag) without a fluid path formed (e.g., when not in the temperature forcing device of FIG. 10), according to an illustrative embodiment.

FIG. 15 illustrates a flexible fluid holder (disposable bag) with a fluid path formed by the temperature forcing device of FIG. 10 when the device is closed. FIG. 16 shows the bag in its normal state without a fluid path formed (e.g., when not in the temperature forcing device of FIG. 10).

Figure 17:
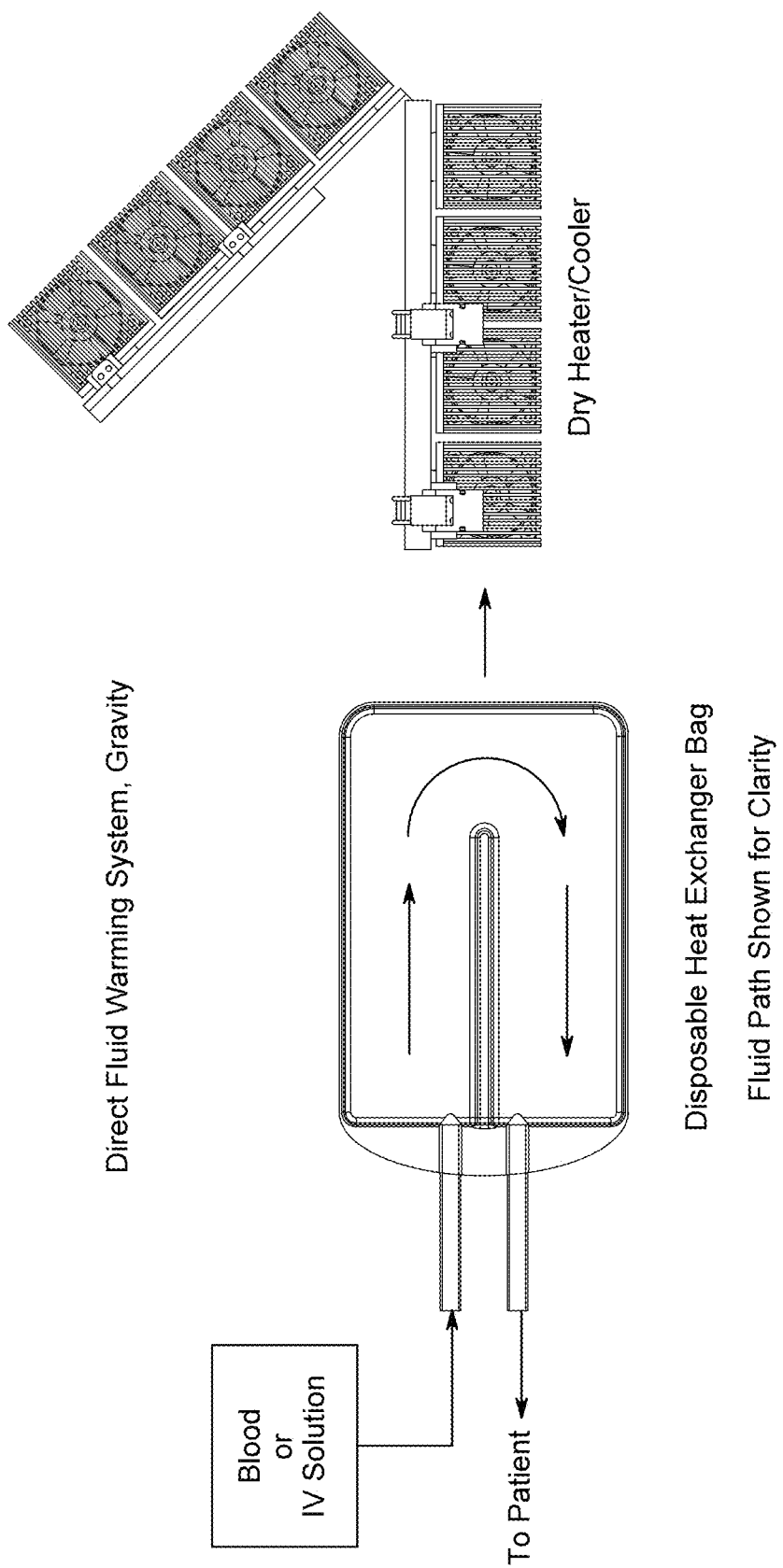
FIG. 17 illustrates a direct fluid warming and/or cooling system with fluid flow provided by gravity, according to an illustrative embodiment.

FIG. 17 illustrates a direct fluid warming and/or cooling system with fluid flow provided by gravity, according to an illustrative embodiment. The fluid depicted is a therapeutic fluid. The fluid enters the inlet of the flexible fluid holder (disposable heat exchanger bag), with channel formed therein when the bag is placed between the top and bottom plates of the temperature forcing device (dry heater/cooler) and those plates are closed together. The fluid is heated and/or cooled by the dry heater cooler as it flows from the inlet to the outlet of the heat exchanger bag, then the fluid is delivered to the patient. At no time does the fluid directly contact the dry heater/cooler.

Figure 18:
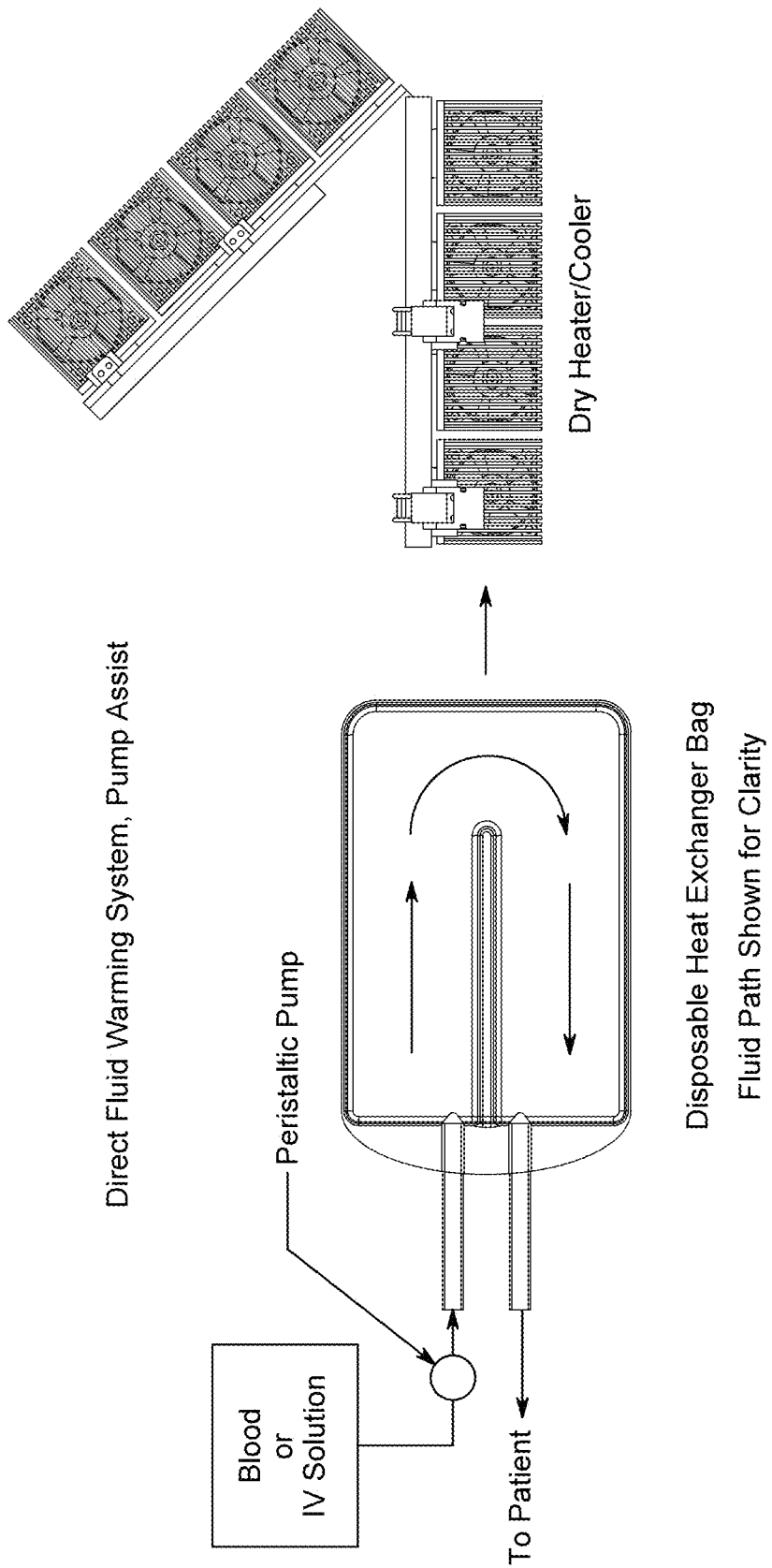
FIG. 18 illustrates a direct fluid warming and/or cooling system with pump assist, according to an illustrative embodiment.

FIG. 18 illustrates a direct fluid warming and/or cooling system with pump assist, according to an illustrative embodiment. This system is identical to that shown in FIG. 17, except that a pump (here, a peristaltic pump) is depicted to assist flow of the therapeutic fluid (e.g., blood or IV solution) through the temperature forcing device. At no time does the fluid directly contact the dry heater/cooler.

Figure 19:
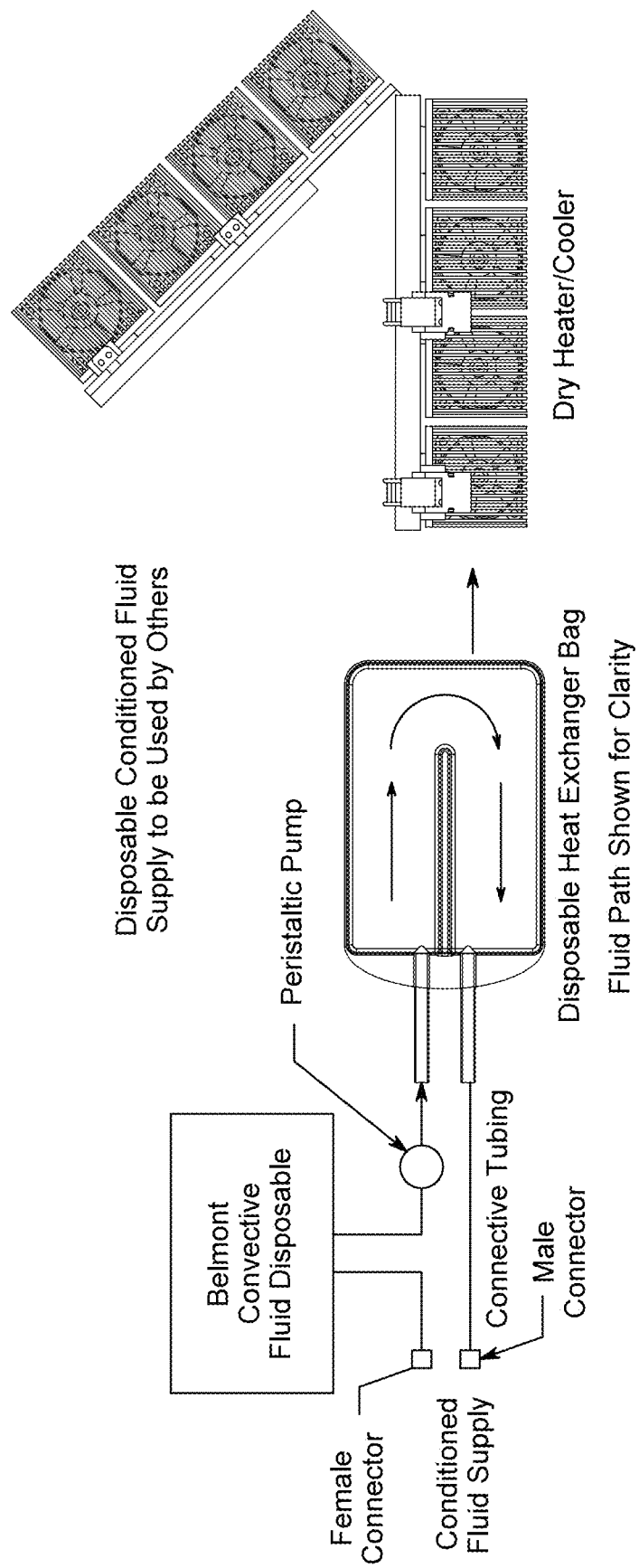
FIG. 19 illustrates a conditioned fluid warming and/or cooling system, according to an illustrative embodiment.

FIG. 19 illustrates a conditioned fluid warming and/or cooling system, according to an illustrative embodiment. Here, conditioned fluid from a supply is pumped through a reservoir (labeled "Belmont Convective Fluid Disposable") and into the disposable heat exchanger bag placed between the top and bottom plates of a temperature forcing device (here, a dry heater/cooler). Upon heating and/or cooling by the temperature forcing device, the conditioned fluid flows through the outlet of the disposable heat exchanger bag and into connective tubing, for use as a temperature-controlled heat exchange fluid in another part of the system. At no time does the fluid directly contact the dry heater/cooler. Furthermore, the entire fluid flow path including the reservoir, the peristaltic pump (if used), the connective tubing, and the heat exchanger bag, can be made to be disposable, further reducing contamination risk.

In some embodiments, the system in accordance with the present disclosure comprises a component that directly, physically contacts the body of a patient for managing a body temperature of the patient. In some embodiments, the component is a blanket, a wrap, or a mattress containing the fluid. In some embodiments, the component may be worn over a portion of the patient's body. For example, the component may be designed so as to cover at least about 30%, 40%, or 50% of the body's surface. The system may stabilize the patient's body temperature, at a desired body core temperature. Such a component may have different forms depending on its intended use. For example, the component may be designed for medical use, either for the purpose of reducing core temperature (e.g., for a patient having a disease with a very high fever), for the purpose of increasing core body temperature (e.g., as a hyperthermia treatment, or after hypothermia treatment), or for both.

In some embodiments, the system may further comprise one or more thermometers or other temperature sensors for detecting the temperature of the circulating fluid and/or the patient's body temperature. In some embodiments, a thermometer (or other temperature sensor) measures temperature of the fluid as it enters the component (e.g., blanket, a wrap, or a mattress). In some embodiments, a thermometer (or other temperature sensor) measures an outlet temperature of the fluid as it exits the component (e.g., blanket, a wrap, or a mattress).

These and other features, aspects and advantages of the present invention will become better understood with reference to the following description and appended claims. The accompanying drawings, which are incorporated in and constitute a part of this specification, illustrate embodiments of the present disclosure and, together with the description, serve to explain the principles of the present embodiments.

Certain Definitions

In order for the present disclosure to be more readily understood, certain terms are first defined below. Additional definitions for the following terms and other terms are set forth throughout the specification.

An apparatus, composition, or method described herein as "comprising" one or more named elements or steps is open-ended, meaning that the named elements or steps are essential, but other elements or steps may be added within the scope of the composition or method. To avoid prolixity, it is also understood that any apparatus, composition, or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any apparatus, composition, or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

As used herein, the term "patient" or "subject" (used interchangeably herein) refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In certain embodiments, a patient is a human. In certain embodiments, a patient is suffering from or susceptible to one or more disorders or conditions. In certain embodiments, a patient displays one or more symptoms of a disorder or condition. In certain embodiments, a patient has been diagnosed with one or more disorders or conditions. In certain embodiments, the disorder or condition is or includes bacterial infection. In certain embodiments, the patient is receiving or has received certain therapy to diagnose and/or to treat a disease, disorder, or condition.

As used herein, the term "substantially" refers to the qualitative condition of exhibiting total or near-total extent or degree of a characteristic or property of interest.

EQUIVALENTS

It is to be understood that while the disclosure has been described in conjunction with the detailed description thereof, the foregoing description is intended to illustrate and not limit the scope of the invention(s). Other aspects, advantages, and modifications are within the scope of the claims.

This written description uses examples to disclose the invention, including the best mode, and also to enable any person skilled in the art to practice the present embodiments, including making and using any devices or systems and performing any incorporated methods. The patentable scope of the present embodiments is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A system for heating and/or cooling a fluid, the system comprising:
    at least one flexible fluid holder;
    a temperature forcing device comprising a bottom plate and a top plate hingedly coupled to the bottom plate, at least one of said bottom plate and said top plate comprising a recess or other area disposed therein or thereupon for receiving the at least one flexible fluid holder, said at least one fluid holder comprising a fluid inlet for receiving the fluid to be heated and/or cooled and a fluid outlet for delivering the heated and/or cooled fluid out of the temperature forcing device;
    at least one fin disposed in at least one of the bottom plate and the top plate;
    a fan to increase a flow of air across the at least one fin; and
    at least one member selected from the group consisting of a blood detector, at least one fluid temperature sensor, a pressure transducer, at least one patient temperature probe, an air detector, and a fluid flow rate detector,
    wherein the at least one flexible fluid holder and the temperature forcing device are arranged such that the fluid being heated and/or cooled does not directly contact the temperature forcing device, thereby eliminating the need for the heater to be sterilized.

2. The system of claim 1, comprising an entirely disposable fluid path,
    wherein the at least one flexible fluid holder forms a portion of the entirely disposable fluid path.

3. The system of claim 2, wherein the at least one fluid holder is mounted to a mounting sheet, and wherein the mounting sheet forms a portion of the entirely disposable fluid path.

4. The system of claim 3, wherein the mounting sheet further comprises:
    angled and/or tapered corners at the end proximate the fluid inlet and fluid outlet.

5. The system of claim 3, wherein the mounting sheet comprises a continuous portion of the fluid holder that does not end up forming the fluid passageways that form once the fluid holder is placed in service within the solid-state device.

6. The system of claim 3, wherein the mounting sheet comprises different material properties than the center portion of the fluid holder.

7. The system of claim 2, wherein the disposable fluid path comprises a single-use disposable fluid path.

8. The system of claim 1, wherein the temperature forcing device comprises a solid state device.

9. The system of claim 1, wherein the flexible fluid holder comprises:
a plastic bag composed of at least one of polyvinyl chloride (PVC), ethylene vinyl acetate (EVAM), polypropylene, and copolyester ether.

10. The system of claim 1, wherein the temperature forcing device comprises:
a compressor.

11. The system of claim 1, wherein at least one of the fluid inlet and the fluid outlet further comprises:
cylindrical tubing that is fluidly connected to other system tubing and/or components via various connection mechanisms.

12. The system of claim 11, wherein at least one connection mechanism of the various connection mechanisms is composed of a material that is harder and/or more rigid than the fluid inlet and/or fluid outlet.

13. The system of claim 1, wherein at least one fin further comprises: a proximal portion disposed close to the respective top plate or bottom plate; a distal portion extending away from the respective top plate or bottom plate; wherein the fin is thinner at the distal portion than at the proximal portion.

14. The system of claim 1, wherein at least one of the fluid inlet and the fluid outlet further comprises:
a tapered portion.

15. The system of claim 1, wherein:
the fluid holder comprises an interior; and
the interior of the fluid holder is formed by two sheets of material that are joined via a seam that extends around a periphery of the fluid holder.

16. The system of claim 1, further comprising:
at least one thermometer that measures temperature of the fluid as it enters the at least one flexible fluid holder;
at least one thermometer that measures temperature of the fluid as it exits the at least one flexible fluid holder.

\* \* \* \* \*